United States Patent [19]

Pantoliano et al.

[11] Patent Number: 4,908,773
[45] Date of Patent: Mar. 13, 1990

[54] COMPUTER DESIGNED STABILIZED PROTEINS AND METHOD FOR PRODUCING SAME

[75] Inventors: Michael W. Pantoliano, Germantown; Robert C. Ladner, Jamesville, both of Md.

[73] Assignee: Genex Corporation, Gaithersburg, Md.

[21] Appl. No.: 34,964

[22] Filed: Apr. 6, 1987

[51] Int. Cl.$^4$ ..................... G06F 15/46; G01N 33/00
[52] U.S. Cl. .................................. 364/496; 364/498; 436/89
[58] Field of Search .................. 436/89; 364/496–500, 364/413

[56] References Cited

U.S. PATENT DOCUMENTS

| | | | |
|---|---|---|---|
| 4,085,443 | 4/1978 | Dubois et al. | 364/900 |
| 4,266,253 | 5/1981 | Matherat | 358/903 |
| 4,414,629 | 9/1983 | Waite | 364/300 |
| 4,668,476 | 5/1987 | Bridgham et al. | 364/500 |
| 4,704,692 | 11/1987 | Ladner | 364/496 |
| 4,719,582 | 1/1988 | Ishida et al. | 364/498 |
| 4,760,025 | 7/1988 | Estell et al. | 435/222 |

FOREIGN PATENT DOCUMENTS 130756  1/1985  European Pat. Off. .
155832  9/1985  European Pat. Off. .

OTHER PUBLICATIONS

Pabo, C. O. et al., *Biochemistry*, 25:5987, Jun. 1986.
Perry, L. J. et al., *Biochemistry*, 25:733, Jul. 1986.
McPhalen, C. A., et al., *FEBS Lett.*, 188:55, Aug. 1985.
Alber, T. et al., *Proc. Natl. Acad. Sci.*, (U.S.A.), 82:747, Feb. 1985.
Vasantha, N. et al., *J. Bacteriol.*, 159:811, Jun. 1984.
Perry, L. J. et al., *Science*, 226:555, Nov. 1984.
Munro, *Nature*, 312:597, Dec. 1984.
Morrison, S. L., *Science*, 229:1202, Sep. 1985.
Oi et al., *Biotechniques*, 4:214, Jan. 1986.
Van Brunt, *Biotechnology*, 4:277, Apr. 1986.
Creative BioMolecules, Inc., Title Page and Abstract, p. 2, Aug. 1984.
Creative BioMolecules, Inc., Phase II Small Business Innovation Research Grant, p. 2, Dec. 1985.
Jones et al., *EMBO J.*, 5:819, Jan. 1986.
Bruccoleri et al., *Biopolymers*, 26:137, Jan. 1987.
Barlow et al., In: "Protein Engineering Applications" (Inouye, et al., Eds.) Academic Press, NY, 1986).
Getzoff et al., In: "Protein Engineering Applications" (Inouye, et al., Eds.), 1986.
Blundell et al., *Nature*, 326:347 (Mar. 1987).
Snow et al., *Proteins*, 1:267 (dated 1986, but believed to have been first available to the public in Apr., 1987).
Moult et al., *Proteins*, 1:267 (dated 1986, but believed to have been first available to the public in Apr. 1987).
Estell et al., *J. Biol. Chem.*, 260:6518–6521, Feb. 1984.
Liao et al., *Proc. Natl. Acad. Sci.*, (U.S.A.) 83:576–580 (1986).
Bryan et al., *Proteins: Structure, Function and Genetics*, 1:326–334, Jan. 1987.
Cunningham et al., *Protein Engineering*, 1:319–325 (1987).
Bryan et al., *Proc. Natl. Acad. Sci.*, (U.S.A.), 83:576–580, Jun. 1986.
Bryan, et al., *J. Cell. Biochem. Suppl.*, 9B:92 (Abstract 0632) (1985).
Pantoliano et al., *Biochemistry*, 26:2077–2092, Dec. 1986.

*Primary Examiner*—Parshotam S. Lall
*Assistant Examiner*—Brian M. Mattson
*Attorney, Agent, or Firm*—Saidman, Sterne, Kessler & Goldstein

[57] ABSTRACT

Proteins, such as enzymes having enhanced stability are designed through the use of a computer method. The method identifies amino acid residues of a protein which may be replaced with a cysteine residue in order to promote the formation of a protein-stabilizing disulfide bond. The computer-designed, stabilized proteins can be produced using recombinant DNA technology.

28 Claims, 6 Drawing Sheets

```
6000       DO (K=1, (Number of amino acids)-1 )
6010       .  LOCATE_STANDARD_PYRAMID_AT_AMINO_ACID_K
6020       .  IF(Location successful)
6030       .  .  DO (L=K+1,(Number of amino acids))
6040       .  .  .  LOCATE_STANDARD_PYRAMID_AT_AMINO_ACID_L
6050       .  .  .  IF(Location successful)
6060       .  .  .  .  CALCULATE_DISTANCE_BETWEEN_PYRAMIDS
6070       .  .  .  .  IF(distance within bounds)
6080       .  .  .  .  .  DO (Jcys =1,Number_observed_cystines)
6090       .  .  .  .  .  .  CALCULATE_RMS_ERROR_VS_K:L
6100       .  .  .  .  .  .  CALCULATE_RMS_ERROR_VS_L:K
6110       .  .  .  .  .  END_DO (Jcys = 1,....
6120       .  .  .  .  .  FIND_CASE_WITH_SMALLEST_RMS_ERROR
6130       .  .  .  .  .  IF(RMS_error below threshold)
6140       .  .  .  .  .  .  WRITE_EXTERNAL_RECORD
6150       .  .  .  .  .  .  SEARCH_FOR_SECOND_BEST_RMS_ERROR
6160       .  .  .  .  .  .  IF(RMS_error below threshold)
6170       .  .  .  .  .  .  .  WRITE_EXTERNAL_RECORD
6180       .  .  .  .  .  .  END_IF(RMS_e.....
6190       .  .  .  .  .  END_IF(RMS_e.....
6200       .  .  .  .  END_IF(dista......
6210       .  .  .  END_IF(Locat.....
6220       .  .  END_DO (L=K+1,...
6230       .  END_IF(Locati...
6240       END_DO (K=1, (Nu....
```

FIG. 5

```
7000    TO LOCATE_STANDARD_PYRAMID_AT_AMINO_ACID_x
7010    .  IF(Amino acid x is a glycine)
7020    .  .  USE_N_CA_C_TO_ADD_CB
7030    .  END_IF glycine
7040    .  IF(too many atoms missing from model)
7042    .  .  location unsuccessful
7044    .  END_IF(too many ....
7050    .  ELSE
7060    .  .  LEAST_SQUARES_FIT_N_CA_CB_C_TO_STANDARD_PYRAMID
7070    .  .  location successful if RMS_error = 0.2A
7080    .  END_ELSE (= all atoms present in model)
7090    END_(TO LOCATE_STANDARD_PYRAMID_AT_AMINO_ACID_x)
```

FIG.6

```
8000    TO CALCULATE_DISTANCE_BETWEEN_PYRAMIDS
8010    .  FIND_CENTER_OF_MASS_OF_PYRAMID_K
8020    .  FIND_CENTER_OF_MASS_OF_PYRAMID_L
8030    .  distance = separation(centers-of-mass)
8040    END_(TO CALCULATE_DISTANCE_BETWEEN_PYRAMIDS)
```

FIG.7

```
9000    TO CALCULATE_RMS_ERROR_VS_pyr#1:pyr#2
9010    .  (N,CA,CB,C) of pyr#1 into slots 1,2,3,4
9020    .  (N,CA,CB,C) of pyr#2 into slots 5,6,7,8
9030    .  LEAST_SQUARES_FIT_EIGHT_ATOMS_TO_CYSTINE_#Jcys
9040    .  REPORT_RMS_ERROR
9050    END_(TO CALCULATE_RMS_ERROR_VS_pyr#1:pyr#2)
```

FIG.8

COMPUTER DESIGNED STABILIZED PROTEINS AND METHOD FOR PRODUCING SAME

BACKGROUND OF THE INVENTION

The present invention pertains to protein molecules which possess enhanced stability and to nucleic acid sequences which encode such proteins. These proteins were designed for enhanced stability using a computer-assisted method.

1. Field of the Invention

The present invention provides a computer-assisted method for designing stable protein molecules.

2. Related Art

Proteins (or polypeptides) are linear polymers of amino acids. Since the polymerization reaction which produces a protein results in the loss of one molecule of water from each amino acid, proteins are often said to be composed of amino acid "residues." Natural protein molecules may contain as many as 20 different types of amino acid residues, each of which contains a distinctive side chain. The particular sequence of amino acid residues in a protein defines the primary sequence of the protein.

Proteins fold into a three-dimensional structure. The folding is determined by the sequence of amino acids and by the protein's environment. The remarkable properties of proteins depend directly from the protein's three-dimensional conformation. Thus, this conformation determines the activity or stability of enzymes, the capacity and specificity of binding proteins, and the structural attributes of receptor molecules. Because the three-dimensional structure of a protein molecule is so significant, it has long been recognized that a means for stabilizing a protein's three-dimensional structure would be highly desirable.

The three-dimensional structure of a protein may be determined in a number of ways. Perhaps the best known way of determining protein structure involves the use of the technique of x-ray crystallography. An excellent general review of this technique can be found in *Physical Biochemistry*, Van Holde, K. E. (Prentice-Hall, N.J. (1971) pp 221-239) Using this technique, it is possible to elucidate three-dimensional structure with remarkable precision. It is also possible to probe the three-dimensional structure of a protein using circular dichroism, light scattering, or by measuring the absorption and emission of radiant energy (Van Holde, *Physical Biochemistry*, Prentice-Hall, N.J. (1971)). Additionally, protein structure may be determined through the use of the techniques of neutron defraction, or by nuclear magnetic resonance (*Physical Chemistry*, 4th Ed. Moore, W. J., Prentice-Hall, N.J. (1972).

The examination of the three-dimensional structure of numerous natural proteins has revealed a number of recurring patterns. Alpha helices, parallel beta sheets, and anti-parallel beta sheets are the most common patterns observed. An excellent description of such protein patterns is provided by Dickerson, R. E., et al. In: *The Structure and Action of Proteins*, W. A. Benjamin, Inc., Calif. (1969). The assignment of each amino acid to one of these patterns defines the secondary structure of the protein. The helices, sheets and turns of a protein's secondary structure pack together to produce the three-dimensional structure of the protein. The three-dimensional structure of many proteins may be characterized as having internal surfaces (directed away from the aqueous environment in which the protein is normally found) and external surfaces (which are in close proximity to the aqueous environment). Through the study of many natural proteins, researchers have discovered that hydrophobic residues (such as tryptophan, phenylalanine, tyrosine, leucine, isoleucine, valine, or methionine) are most frequently found on the internal surface of protein molecules. In contrast, hydrophilic residues (such as asparate, asparagine, glutamate, glutamine, lysine, arginine, histidine, serine, threonine, glycine, and proline) are most frequently found on the external protein surface. The amino acids alanine, glycine, serine and threonine are encountered with equal frequency on both the internal and external protein surfaces.

Proteins exist in a dynamic equilibrium between a folded, ordered state and an unfolded, disordered state. This equilibrium in part reflects the interactions between the side chains of amino acid residues which tend to stabilize the protein's structure, and, on the other hand, those thermodynamic forces which tend to promote the randomization of the molecule.

The amino acid side chain interactions which promote protein folding and confer catalytic activity fall into two classes. The interactions may be caused by weak forces (e.g., hydrogen bonds) between the side chains of different amino acid residues. Alternatively, they may be caused by direct covalent bonding between the sulfhydryl groups of two cysteine amino acid residues. Such a bond is known as a "disulfide" bond.

When a protein is synthesized, any cysteine residues present contain free sulfhydryl groups (—SH). When two sulfhydryl groups in close proximity are mildly oxidized, disulfide bonds (—S—S—) may form, thereby crosslinking the polypeptide chain. The formation of this chemical bond is said to convert two "cysteine" residues into a "cystine" residue. Thus "cysteine" residues differ from a "cystine" residue in that the former molecules contain sulfur atoms which are covalently bonded to hydrogen, whereas the latter molecule contains a sulfur atom which is covalently bonded to a second sulfur atom.

A disulfide bond may stabilize the folded state of the protein relative to its unfolded state. The disulfide bond accomplishes such a stabilization by holding together the two cysteine residues in close proximity. Without the disulfide bond, these residues would be in close proximity in the unfolded state only a small fraction of the time. This restriction of the conformational entropy (disorder) of the unfolded state destabilizes the unfolded state and thus shifts the equilibrium to favor the folded state. The effect of the disulfide bond on the folded state is more difficult to predict. It could increase, decrease or have no effect on the free energy of the folded state. Increasing the free energy of the folded state may lead to a destabilization of the protein, which would tend to cause unfolding. Importantly, the cysteine residues which participate in a disulfide bond need not be located near to one another in a protein's primary amino acid sequence.

One potential way of increasing the stability of a protein is to introduce new disulfide bonds into that protein. Thus, one potential application of recombinant DNA technology to the stabilization of proteins involves the introduction of cysteine residues to produce intraprotein disulfide bonds. There are two ways in which cysteine residues may be introduced into a protein: (1) through a replacement-exchange with one of the protein's normally occurring amino acid residues, or (2) an insertion of a cysteine between two existing amino acid residues.

Although the principles of recombinant DNA technology permit the introduction of new cysteine residues into a protein, they do not provide the researcher with any suggestion of where the introduced cysteine residues of the disulfide bond should be placed, or which amino acid(s) should be exchanged by such a replacement. Because of the substantial size and complexity of protein molecules, an evaluation of potential sites for disulfide bond linkages is exceedingly complex. Recently, investigators have employed computers and computer graphics displays as an aid for assessing the appropriateness of potential linkage sites (Perry, L. J., & Wetzel, R., *Science*, 226:555-557 (1984); Pabo, C. O., et al., *Biochemistry*, 25:5987-5991 (1986); Bott, R., et al., European Patent Application Ser. No. 130,756; Perry, L. J., & Wetzel, R., *Biochemistry*, 25:733-739 (1986); Wetzel, R. B., European Patent Application Ser. No. 155,832). The methods developed by Wetzel and co-workers permit one to project the three-dimensional conformation of a protein onto a computer screen and to simulate the effect which a disulfide bond might have on the protein's structure. Although these methods facilitate the design of more stable proteins, the researcher must still select the amino acid residues which are to be replaced by the cysteine residues of the disulfide bond. Hence, a substantial amount of guess work and trial and error analysis are still required. A need, therefore, still exists where a method which will assist the user in selecting potential disulfide bond linkage sites.

SUMMARY OF THE INVENTION

One goal of the present invention is to provide a method for determining whether the active folded state of a protein would be stabilized by the presence of a disulfide bond between particular regions of the protein molecule. The present invention accomplishes this goal through the development of a novel method for selecting sites in natural proteins where the introduction of a novel disulfide linkage will have a high probability for stabilizing a particular protein. In detail, the invention pertains to a method for evaluating a protein's structure to determine whether the protein contains at least two target amino acid residues, the replacement of at least one of which with a cysteine residue would be sufficient to permit the formation of at least one potentially protein-stabilizing disulfide bond; the method comprising the steps of:

(a) comparing the distance between the centers-of-mass of two candidate target amino acid residues with the distance between the centers-of-mass of the cysteine residues of a disulfide bond;

(b) calculating the error obtained when a known disulfide bond is superimposed on the two candidate target amino acid residues; and (c) using the comparisons (a) and (b) to determine whether the protein contains the at least two target amino acid residues, the replacement of at least one of which with a cysteine residue is sufficient to permit the formation of a potentially protein-stabilizing disulfide bond.

The invention also pertains to a method for producing a protein having a potentially stabilizing disulfide bond which comprises:

(a) using the above-described method to identify at least one target amino acid residue of the protein which could be replaced by a cysteine residue thereby permitting the formation of a potentially protein-stabilizing disulfide bond, and (b) producing a protein molecule wherein the identified target amino acid residue has been replaced with a cysteine residue, the replacement permitting the formation of the potentially protein-stabilizing disulfide bond.

The invention also includes the method of producing a stabilized protein molecule comprising:

(a) using the above-described method to identify at least one target amino acid residue of the protein which could be replaced by a cysteine residue thereby permitting the formation of a potentially protein-stabilizing disulfide bond, (b) producing a protein molecule wherein the identified target amino acid residue has been replaced with a cysteine residue, the replacement permitting the formation of the potentially protein-stabilizing disulfide bond, and (c) forming the disulfide bond.

The invention also includes a method for producing a protein having a potentially protein-stabilizing disulfide bond which comprises:

(a) using a computer based method to evaluate the protein's structure to determine whether the protein contains at least two target amino acid residues, the replacement of at least one of which with a cysteine residue would be sufficient to permit the formation of at least one potentially protein-stabilizing disulfide bridge; the method comprising the steps:

(1) examining each selected pair of amino acids in the protein to determine if they contain certain atoms whose relative three-dimensional positions possess a geometric conformation similar to the corresponding atoms of a known disulfide bridge, (2) examining any pair of amino acids found to contain the certain atoms identified in step (1) to determine whether the new atoms of a possible disulfide linkage can be accommodated without creating unacceptable steric hindrance, (3) permitting an expert operator (i) to view any possible disulfide linkage which can be accommodated without altering the tertiary conformation of the protein molecule, and (ii) to rank the viewed possible disulfide linkages from most likely to stabilize an engineered protein, to least likely to stabilize the protein, and (4) evaluating the ranked proteins according to expert rule criterion; and (b) producing a protein molecule wherein at least one of the target amino acid residues has been replaced by a cysteine residue, the replacement permitting the formation of a potentially protein-stabilizing disulfide bond.

The invention additionally includes a protein of increased stability produced by the above method.

The invention further includes a nucleic acid sequence which encodes a protein of increased stability produced by the above method.

BRIEF DESCRIPTION OF THE FIGURES

The invention may be better understood with reference to the following description read in conjunction with the following figures.

The following legends are used in the figure: 1. Preparation of library of known disulfide bonds; 2. Selection of a pair of candidate amino acid residues; 3. Calculation of the distance between the centers-of-mass of the candidate residues; 4. Determination of whether the calculated distance is within library range; 5. Calculation of extent of fit between atoms of selected residues and disulfide bonds of library; 6. Determination of whether fit is acceptable; 7. Discard selected pair; 8. Record made of fit; 9. Calculation of second best fit; 10. Determination of whether second best fit is acceptable; 11. Record made of second best fit; 12. Discard second best fit; 13. Prepare a list of records; 14. Scan list of recorded fits; 15. Calculation of number and kind of short contacts; 16. Determination of whether number and kind of short contacts are acceptable; 17. Discard selected pairs; 18. Interactive 3-D graphics display of possible candidate pairs; 19. User initiated ranking of candidate pairs; 20. Expert rule criteria analysis; 21. Identification of potentially protein-stabilizing disulfide bond.

Figure 2:
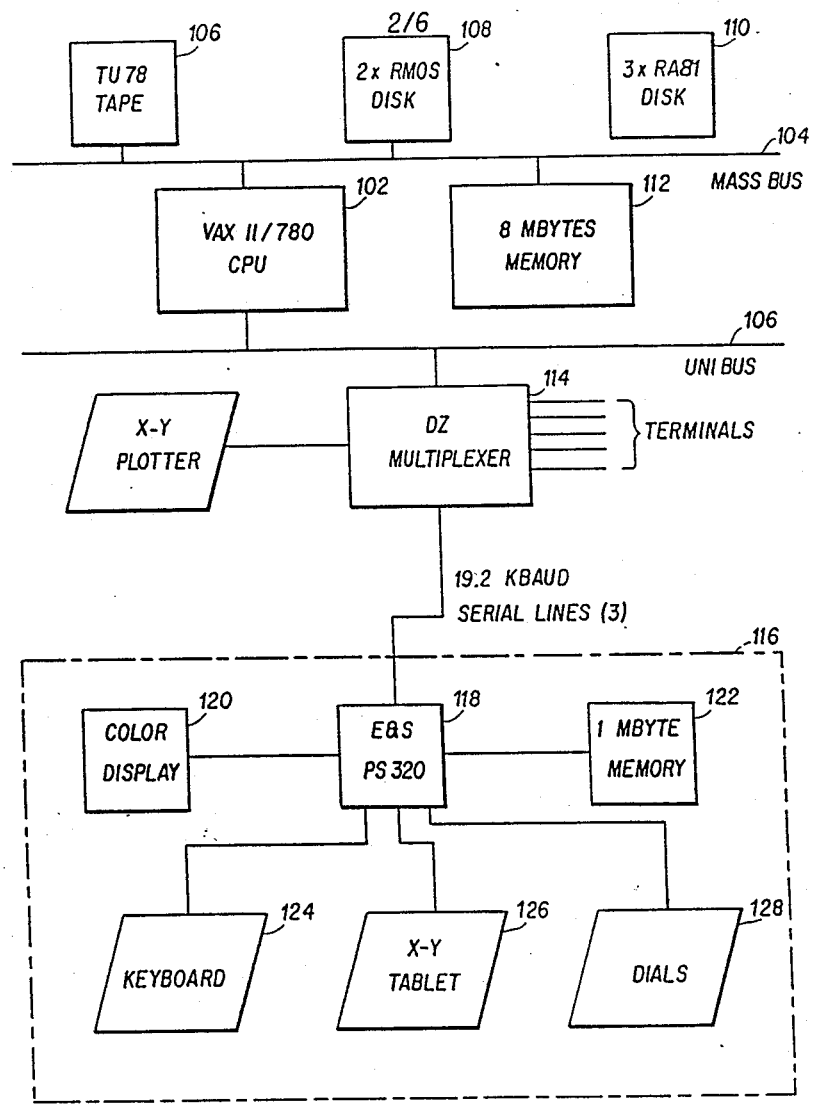

FIG. 2 shows a block diagram of computer hardware suitable for use with the computer based method of the invention.

Figure 3:
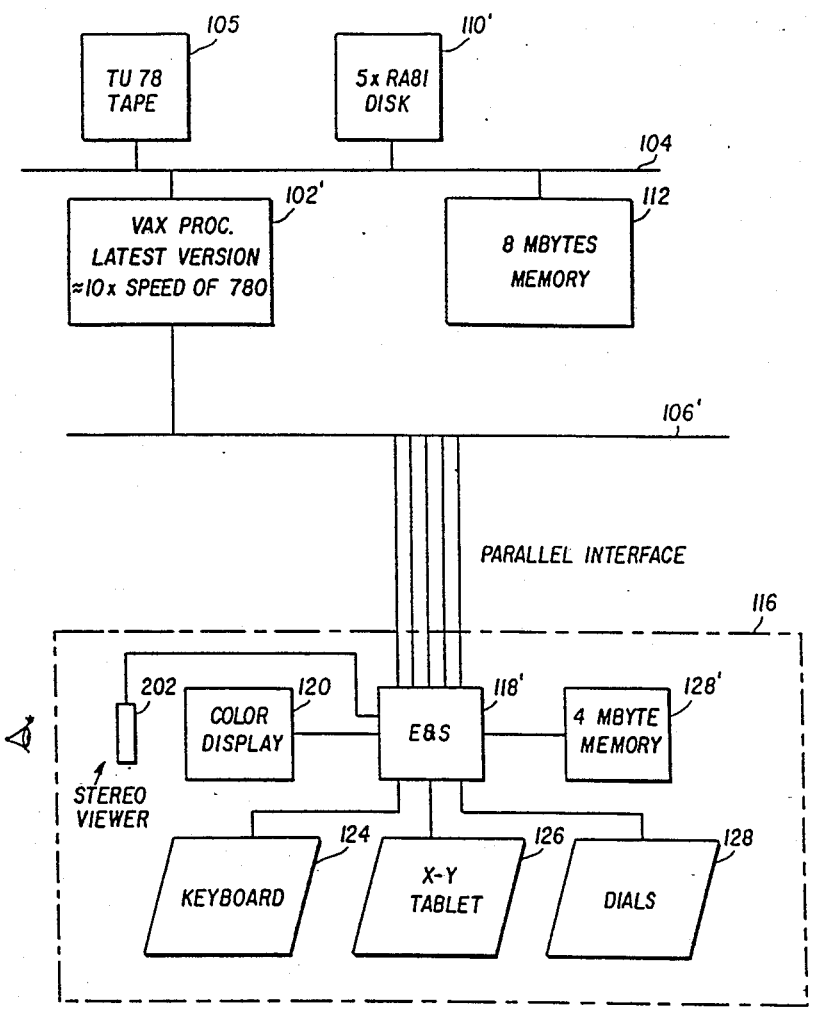

FIG. 3 shows a block diagram of a preferred version of computer hardware suitable for use with the computer based method of the invention.

Figure 4:
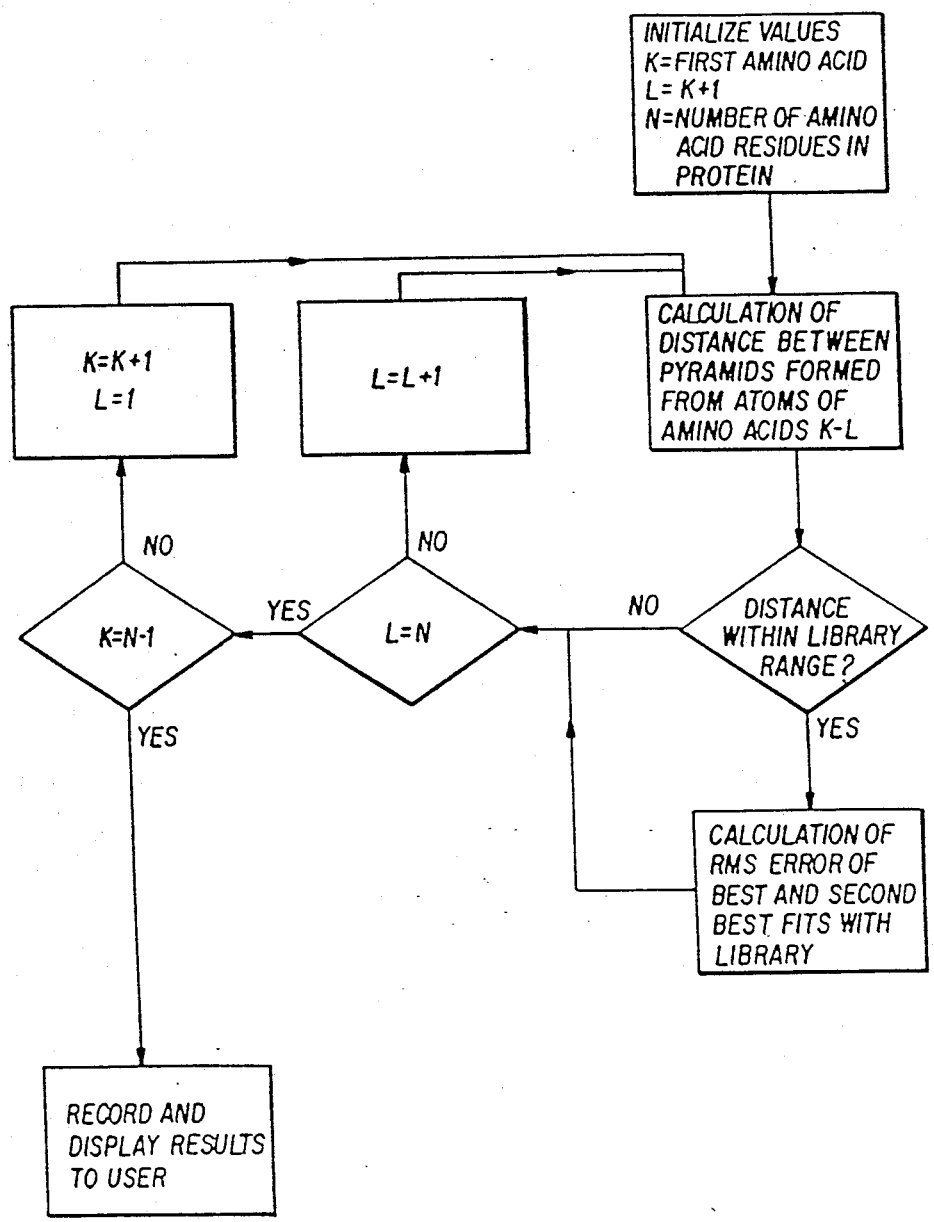

FIG. 4 shows a diagrammatical representation of the algorithm for selecting a potential disulfide bond sites of the invention.

FIG. 5 shows a representation of a computer program displaying the steps of the algorithm of the computer based method of the invention.

FIG. 6 shows a representation of the "Locate Standard Pyramid at Amino Acid X" procedure of the computer based method of the invention.

FIG. 7 shows a representation of the "Calculate Distance Between Pyramids" procedure of the computer based method of the invention.

FIG. 8 shows a representation of the "Calculate RMS Error vs. pyr#1:pyr#2" procedure of the computer based method of the invention.

DESCRIPTION OF THE PREFERRED EMBODIMENTS

Table of Contents

I. Brief Overview of the Invention

A. Thermodynamic Considerations
B. The Five General Steps of the Invention
  1. The First General Step
  2. The Second General Step
  3. The Third General Step
  4. The Fourth General Step
  5. The Fifth General Step II. The Invention in Detail A. The Five General Steps of the Invention
B. The Preparation of the Library of Disulfide Linkages
C. The Selection of Sites to Stabilize a Protein
  1. The Process in General
  2. The Process in Detail
D. The Elimination of Potential Candidates
  1. Elimination of Candidates Based Upon Considerations of Steric Interactions
  2. Elimination of Candidates Based Upon Considerations of Sequence Conservation
E. Recombinant DNA Manipulations
  1. Production of Engineered Proteins
  2. Production of Engineered Proteins by in vitro Mutagenesis of DNA

I. BRIEF OVERVIEW OF THE INVENTION

The invention provides a method for identifying possible sites within a protein molecule at which cysteine residues might be introduced to replace the normally present amino acid residues. These cysteine residues would then be permitted to form disulfide bonds with each other. By correctly selecting the sites for cysteine incorporation, these disulfide bonds determined by the invention will add to the stability of the folded active protein conformation. The methods and proteins of the present invention are disclosed in co-pending, commonly assigned U.S. patent application Ser. No. 034,966, filed concurrently with this application by Pantoliano, M. W., et al.

The present invention provides a method for evaluating a protein's structure to determine whether the protein contains at least two target amino acid residues. An amino acid residue is considered to be a "target" residue if its replacement with a cysteine residue would be sufficient to permit the formation of at least one potentially-stabilizing disulfide bond. As used herein, the terms disulfide bond, disulfide linkage, and disulfide bridge are meant to be interchangeable and equivalent. An amino acid which is being evaluated to determine whether it may serve as a target amino acid residue is termed a "candidate target" amino acid residue. Any amino acid residue of protein may, thus, be considered as a "candidate target" amino acid residue; however, only certain amino acid residues will fulfill the requirements of a "target" residue.

To accomplish the above-described goals, the present invention employs a computer based method for determining and displaying possible sites within natural or engineered proteins where cysteine residues could be inserted to replace the naturally-occurring amino acid residue so that a disulfide linkage would form when the modified protein was mildly oxidized. If the original protein contains one cysteine suitably related to another amino acid, it may be sufficient to change only one amino acid to produce the novel disulfide linkage. In most cases, however, it will be necessary to introduce two cysteine residues into the engineered protein. The original natural protein is referred to as the "wild-type protein." In contrast, the protein which contains the introduced cysteine residues is referred to as the "engineered protein." The terms "disulfide bridge", "disulfide bond", and "cystine" are meant to be equivalent and to describe the structure formed from the disulfide bonding of two cysteine residues to one another.

A. Thermodynamic Considerations

Although disulfide bonds possess the capacity for stabilizing the folded state of a protein molecule, the presence of a disulfide bond does not control whether the bond will promote protein folding or unfolding. In order to determine the effect of a disulfide bond on protein structure, it is necessary to consider the effects of that bond on the free energy of the folded protein molecule and the unfolded protein molecule.

The free energy of a molecule is a thermodynamic measure of the conformation of a molecule. To increase the stability of a protein, one must either lower the free energy of the folded state, or raise the free energy of the unfolded state. The free energy of a molecule is determined from the formula:

$$\Delta G = \Delta H - T(\Delta S)$$

where $\Delta G$ represents the free energy of protein unfolding (folded$\rightleftharpoons$unfolded), $\Delta H$ represents the change in enthalpy of reaction, T represents the temperature, and $\Delta S$ represents the change in free entropy. At low temperature, the value $\Delta H$ exceeds the product of temperature and $\Delta S$. Thus $\Delta G$ is a positive value and the folded state of the protein will predominate. In contrast, as the temperature is raised the product of temperature and free entropy eventually exceeds the value of $\Delta H$ and causes $\Delta G$ to become a negative number. When $\Delta G$ is less than zero, protein unfolding will predominate. Thus, if one could decrease the value of $\Delta S$, the folded state would be more stable even at higher temperatures. Lowering $\Delta S$ may be accomplished by providing either more disorder within the folded state, or by decreasing the disorder of the unfolded state.

The introduction of disulfide bonds may increase the stability of natural proteins by lowering the disorder of the unfolded protein state. Amino acids that are distant in sequence would normally be free to be far apart in the unfolded state, but this freedom would be lost if the residues were linked by a disulfide bond. For this linkage to actually stabilize the folded state, the disulfide bond must not adversely affect $\Delta H$ or impose additional order on the folded state. This means that the disulfide bond must fit into the normal protein conformation without straining it. Importantly, the further the two cysteines residues are from one another in the primary protein structure, the greater will be the affect upon the $\Delta S$. Thus, linking two distant cysteine residues should destabilize the unfolded protein state much more than a similar linkage between two closely adjacent cysteine residues.

The invention may be operated on a conventional mini-computer system having storage devices capable of storing the Brookhaven protein data bank or an equivalent data base, various applications programs utilized by the invention, and the parameters of the possible candidates that are being evaluated.

The mini-computer CPU is connected by a suitable bus to an interactive computer graphics display system. Typically, the interactive computer graphics display system comprises a display terminal with resident three-dimensional application software and associated input and output devices, such as X-Y plotters, position control devices (potentiometers, an X-Y tablet, or a mouse), and keyboard.

The interactive computer graphics display system allows an operator to view the chemical structures being evaluated in the design process of the invention. Graphics and programs are used to evaluate the possible conflicts between new disulfide bridges and retained atoms of the wild-type protein.

B. The Five General Steps of the Computer Based Method

It is initially necessary to select a particular protein molecule whose enhanced stability is desired. The three-dimensional structure of the protein molecule is determined by means known in the art. Once this structure has been ascertained it is possible to employ the novel method of the present invention.

1. The First General Step

The first general step of the computer based method of the invention involves the compilation of a library of acceptable geometries which are defined by disulfide linkages between regions of protein main chain. Such a library can be constructed from the Brookhaven Protein Data Bank (BPDB) (Brookhaven Protein Date Base, Chemistry Dept., Brookhaven National Laboratory, Upton, N.Y. 11973) or equivalent data bases.

To produce such a library, one ascertains the bond distances and bond angles associated with all atoms of the two cysteine residues of disulfide bonds which are present in proteins whose three-dimensional structure has previously been elucidated. Each entry of this library must have acceptable bond distances and bond angles and must differ in internal geometry from all other entries in the library. The construction of this library need not be repeated unless the library is to be enlarged.

For each disulfide bond entered into the library, it is necessary to record the positions of all 14 non-hydrogen atoms of the disulfide bonds (seven from each cysteine; main chain N, alpha C, beta C, S, carbonyl C, carbonyl O, and N of next residue). From these coordinates, one can calculate the dihedral angle along the bond which joins the two sulfur atoms. This angle is called "CHI$_3$" (CHI$_3$ as used in this application arbitrarily has the opposite sign from the usual CHI$_3$ defined in the literature, i.e., 244° = 116°). Such bond angles are referred to as the "characterizing" bond angles of a disulfide bond.

It has been noted by the inventors that there are cases in which two or more observed disulfide bridges can be superimposed to high degree of accuracy considering the atoms N, alpha C, beta C, and carbonyl C on each side of the disulfide bridge, but that the S atoms do not match at all well. In such cases, one disulfide bridge has CHI$_3$ near 90 degrees while the other has CHI$_3$ near $-90$ degrees. When the main-chain atoms are in such a relationship, the geometry of the disulfide group is determined by the surrounding atoms.

2. The Second General Step

The second general step of the computer based method of the invention involves examining each pair of amino acid residues in the protein of interest to see if they contain certain atoms whose relative three-dimensional positions possess the same geometric conformation as the corresponding atoms of some known disulfide bridge. This examination is done automatically by the computer program, which evaluates the library prepared in the first general step of the present invention. The atoms checked in this step are the main-chain nitrogen, the alpha carbon, the beta carbon, and the carbonyl carbon of the two amino acids of the selected pair. Within each amino acid, these four atoms form a pyramid with the alpha carbon at the apex and with no easily-changed internal degrees of freedom.

The computer program which implements the second general step is broken into two phases. The first phase examines the distance between the centers-of-mass of the pyramids formed within each of the two amino acids of the selected pair. If the distance between the two centers-of-mass is greater than the largest known distance of any of the disulfide linkages in the library, or smaller than the smallest known distance of any of the disulfide linkages in the library, then the selected pair of residues is discarded and the next pair of residues is considered. Alternatively, if the distance between the centers-of-mass of the two residues fall within the range of inter-pyramid distances in the library then the second phase of the second general step is executed for this pair of residues.

In the second phase of the second general step of the present invention, the eight atoms forming the pyramids of the two residues in question are considered as a single group having eight three-dimensional coordinates. The structure of this 8-atom group is compared (according to the method of least squares) to each of the different disulfide bridges contained in the library. The root-mean-squared (RMS) error for the fit of the selected amino acid pair as compared to each different observed disulfide bond in the library is recorded in computer memory. If for at least one observed disulfide bridge, the RMS error falls below a preset limit then the residue pair in question is recorded as passing the second general step. This preset limit may vary between 0.3–0.6 Å and is preferably set to a value within the range 0.4–0.5 Å. When a residue pair passes the second general step an external record is provided which indicates the amino acid pair in question, the identity of the disulfide bond which possess the similar geometry, the RMS error of the analysis and the value of $CHI_3$ of the fit. After this information has been recorded, the computer program searches for a second fit with the restriction that the $CHI_3$ must differ from the $CHI_3$ of the best fit by some preset amount (preferably between 15–25 degrees). If such a second-best fit has a RMS error which is below the threshold written above, then a second record is written indicating the amino acid pair involved, the disulfide bond which provides the second best fit, the RMS error of this second-best fit, and the value of $CHI_3$ of the second-best fit.

If the RMS error does not fall below the preset limit for any of the recorded disulfide linkages, then the current residue pair is rejected and the next pair is examined. For example, with a particular protein of 141 amino acids (such as for example staphylococcal nuclease), 387 amino acid pairs will pass phase one of the second general step. However, only 27 sites will pass phase two of step two and thus be subject to further consideration. The number of sites to be tested will rise as the square of the number of amino acids which comprise the protein, however, the number of good candidates will rise only linearly with this number. The linear rise in the number of good candidates is a result of the limited number of close neighbors which any residue can have.

3. The Third General Step

In the third general step of the computer based method, the sites listed in the second general step are examined by a computer program to see if the new atoms of the disulfide linkage can be accommodated without altering the tertiary conformation of the protein molecule. Specifically, the new sulfurs of the disulfide bond (to be incorporated into the protein molecule) are positioned according to the observed disulfide which matched best at the site in question in step two. If either or both of the wild-type amino acids are glycines, beta carbons are added as needed. The distance between the sulfurs (and carbons, if new) and all nearby atoms are calculated and a list of distances shorter than physically reasonable (i.e., a list of possible steric contacts) is recorded. This list is divided into two categories based upon the kind of interaction involved: interactions with main-chain atoms and interactions with side-chain atoms (the beta carbon is included as a main chain atom because it cannot be moved by rotation about the side-chain bonds). To allow for flexibility in the protein and for possible errors in the coordinates recorded in the library, a separation distance at which a contact is taken as unreasonably short is set to some preset amount. This preset amount is smaller than the sum of the van der Waals radii of the atoms in question. This preset value is preferably between 0.4–0.6 Å, however other values could be used.

Because protein side-chains can rearrange more easily than the main chain, short contacts between atoms of the disulfide bond, and main-chain atoms are considered as potentially more damaging than contacts with side-chain atoms. The sites selected in step two are ordered according to the number of main-chain short contacts. If several sites have identical numbers of main-chain short contacts, these sites are ordered according to the number of side-chain short contacts.

In one embodiment, all sites selected in general step two are passed through to step four with a notation of how many sterically unacceptable contacts exist in each category. An expert user reviews this list and excludes sites with excessive numbers of such contacts.

4. The Fourth General Step

In the fourth general step of the computer based method, an expert operator uses an interactive three-dimensional computer graphics display to view each of the disulfide bond candidates and to rank them from those most likely to stabilize an engineered protein (relative to the wild-type protein), to those least likely to stabilize the protein. This ranking is done by considering:

1. the number of short contacts recorded in general step three,
2. whether any of these short contacts can be relieved by slight changes in side-chain or main-chain conformation, or
3. the length of the polypeptide loop created by the disulfide bridge.

5. The Fifth General Step

In the fifth general step of the present invention, sequences of proteins evolutionarily related to the wild-type protein are used to discover which amino acids may be most easily altered without seriously reducing the stability of the protein. If many sequences are available for similar proteins from a variety of sources, it may be observed that certain residues are strongly conserved in evolution. This conservation will indicate that, in a given location, one particular amino acid is strongly preferred to give an active, stable protein. At many other locations, however, a plurality of amino acids may be acceptable. This information is used to further rank the candidates to determine which of the possible pairs of residues are most likely to give a stabilizing disulfide bridge. If all other factors are equal, those sites which involve no conserved amino acids are much more likely to give a stabilized disulfide bridge than a site which involves one conserved amino acid, which in turn is much more likely to give a stabilizing disulfide bridge than a site which involves two conserved amino acids.

The elected candidates provide potential sites at which pairs of cysteine residues may be introduced. Mild oxidation of the resulting engineered proteins will give rise to proteins containing disulfide bridges. The method of selecting the sites described in general steps 1–5 makes it highly likely that the resulting engineered proteins will have the same tertiary structure and biological activity as the initial wild-type protein. Moreover, it is highly likely that the engineered proteins will be more stable with regard to agents which cause proteins to unfold (i.e., elevated temperature, altered pH, organic solvents, detergents, or chaotropic salts).

The parameters of the candidates can be stored for later use. They can also be provided by the user either visually or recorded on a suitable medium (paper, magnetic tape, color slides, CRT, etc). The results of the various steps utilized in the analysis can be stored for later use or examination. The present invention can be programmed so that certain expert rules are utilized to eliminate unsuitable candidates before they are presented to the operator. These expert rules can be modified based on experimental data as more proteins are modified by introduction of disulfide bridges, or as more natural proteins containing disulfide bridges are added to the data base used in general step one.

II. THE INVENTION IN DETAIL

A. The Five General Steps of the Invention

The present invention enables one to identify possible residues which, if replaced by cysteines, might result in the formation of a potentially protein stabilizing disulfide bond. The above-described general steps of the invention may be performed manually, in a semi-automated process or more preferably with the aid of a computer. The best mode for performing the general steps of the invention involves the use of a computer. The computer-assisted method of the best mode is described in related, co-pending, commonly assigned U.S. Pat. No. 4,853,871, filed concurrently with this application by Pantoliano, M. W., et al.

B. The Preparation of the Library of Disulfide Linkages

The Brookhaven Protein Data Bank (BPDB) contains structures for between 250 and 300 proteins. Many of these structures contain disulfide bridges. Because this collection of structures has been obtained from many different laboratories over several years, there is substantial variation in the quality of structures. Most protein structures are refined against diffraction data subject to constraints or restraints. Many proteins do not diffract x-rays very well and consequently insufficient data exists to determine the position of each atom. Furthermore, until quite recently collection of protein diffraction data was very laborious so that crystallographers often did not collect al the data that could be collected.

Crystallographers generally assume that all bond distances and angles are the same as or very close to the distances and angles determined in small-molecule structures where every atom can be localized very accurately. These added data make it possible to construct models of proteins in which each non-hydrogen atom is represented by an x-y-z triplet plus an isotropic temperature factor.

Figure 1:
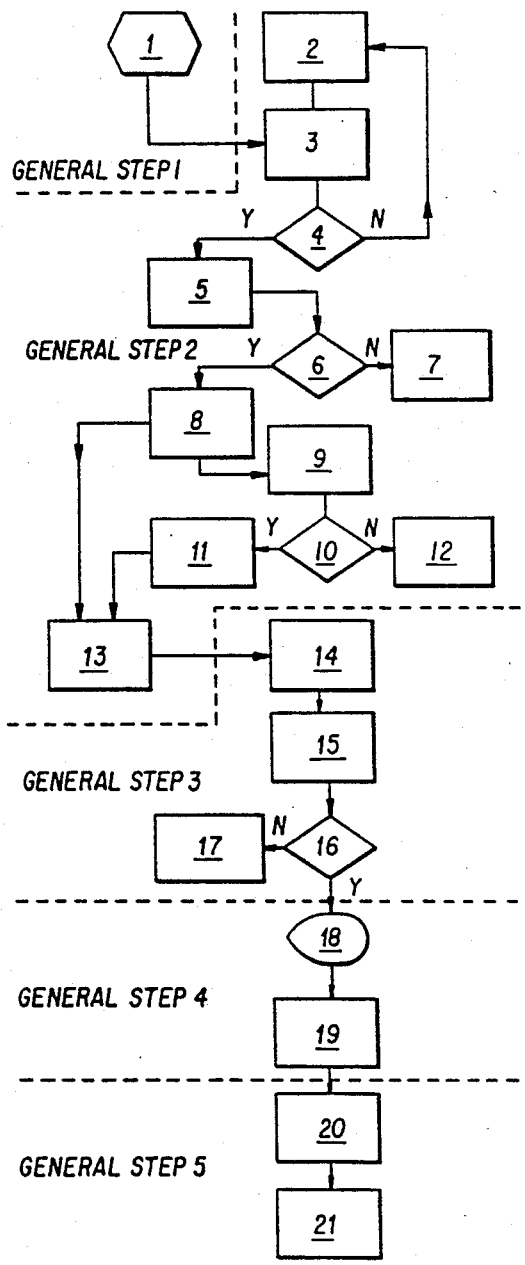
FIG. 1 shows in diagrammatical form the five general steps of the computer based method of the invention.

As the methods of the present invention utilize the geometric relationship between two amino acids which might be connected by a disulfide bridge, the most important point to determine about each reported disulfide bridge is whether the report is correct. The eight main-chain atoms have 24 degrees of freedom. Least-squares fitting of a standard pyramid (containing the nitrogen, carbonyl carbon, alpha carbon, and beta carbon of an amino acid) at each end filters out most of the noise in the report coordinates. Finally the six degrees of freedom relating the two standard pyramids are The five general steps of the computer based method are diagrammed in FIG. 1. A block diagram of the hardware aspects of the computer based method is found in FIG. 2. A control processing unit (CPU) 102 is connected to a first bus (designated massbus 104) and td a second bus (designated Unibus 106). A suitable form for CPU 102 is a model Vax 11/780 made by Digital Equipment Corporation of Maynard, Mass. Any suitable type of CPU, however, can be used.

Bus 104 connects CPU 102 to a plurality of storage devices. In the best mode, these storage devices include a tape drive unit 106. The tape drive unit 106 can be used, for example, to load into the system the data base of the amino acid sequences whose three dimensional structures are known. A suitable form for tape drive 106 is a Digital Equipment Corporation model TU 78 drive, which operates at 125 inches per second, and has a 1600–6250 bit per inch (BPI) dual capability. Any suitable type of tape drive can be used, however.

Another storage device is a pair of hard disk units labeled generally by reference numeral 108. A suitable form for disk drive 108 comprises two Digital Equipment Corporation RM$\phi$5 disk drives having, for example, 256 Moytes of storage per disk. Another disk drive system is also provided in the serial processor mode and is labeled by reference numeral 110. This disk drive system is also connected to CPU 102 by bus 104. A suitable form for the disk system 110 comprises three Digital Equipment Corporation model Ra 81 hard disk drives having, for example, 450 Mbytes of storage per disk.

Dynamic random access memory is also provided by a memory stage 112 also connected to CFU 102 by bus 104. Any suitable type of dynamic memory storage device can be used. In the serial processor mode, the memory is made up of a plurality of semi-conductor storage devices found in a DEC model ECC memory unit. Any suitable type of dynamic memory can be employed.

The disk drives 108 and 110 store several different blocks of information. For example, they store the data base containing the amino acid sequences and structures that are read in by the tape drive 106. They also store the application software package required to search the data base in accordance with the procedures of the present invention. They also store the documentation and executables of the software. The hypothetical molecules that are produced and structurally examined by the present invention are represented in the same format used to represent the protein structures in the data base. Using this format, these hypothetical molecules are also stored by the disk drives 108 and 110 for use during the structural design process and for subsequent use after the process has been completed.

A Digital Equipment Corporation VAX/VMS (DEC Trademark) operating system allows for multiple users and assures file system integrity. It provides virtual memory, which relieves the programmer of having to worry about the amount of memory that is used. Initial software was developed under versions 3.0 to 3.2 of the VAX/VMS operating system. The current embodiment presently is running on version 4.4. DEC editors and FORTRAN compiler were utilized.

The CPU 102 is connected by bus 106 to a multiplexer 114. The multiplexer allows a plurality of devices to be connected to the CPU 102 via bus 106. A suitable form for multiplexer 114 is a Digital Equipment Corporation model Dz 16 terminal multiplexer. In the preferred embodiment, two of these multiplexers are used. The multiplexer 114 supports terminals (not shown in FIG. 2) and the serial communications (at 19.2 Kbaud, for example) to the computer-graphics display system indicated by the dash lined box 116.

The computer-graphics display system 116 includes an electronics stage 118. The electronic stage 118 is used for receiving the visual image prepared by CPU 102 and for displaying it to the user on a display (typically one involving color) 120. The electronic stage 118 in connection with the associated subsystems of the computer-graphics display system 116 provide for local control of specific functions, as described below. A suitable form of the electronics system 118 is a model PS 320 made by Evans & Sutherland Corp. of Salt Lake City, Utah. A suitable form for the display 120 is either a 25-inch color monitor or a 19-inch color monitor from Evans & Sutherland.

Dynamic random access memory 122 is connected to the electronic stage 118. Memory 122 allows the electronic system 118 to provide the local control of the image discussed below. In addition, keyboard 124 of conventional design is connected to the electronic stage 118, as is an x/y tablet 126 and a plurality of dials 128. The keyboard 124, x/y tablet 126, and dials 128 in the serial processor mode are also obtained from Evans & Sutherland.

The computer generated graphics system 116, as discussed above, receives from CPU 102 the image to be displayed. It provides local control over the displayed image so that specific desired user initiated functions can be performed, such as:

(1) zoom capacity (so as to increase or decrease the size of the image being displayed);
(2) clipping capacity (where the sides, front or back of the image being displayed are removed);
(3) intensity depth queuing (where objects further away from the viewer are made dimmer so as to provide a desired depth effect in the image being displayed);
(4) translation capacity (allowing translation of the image in any of the three axes of the coordinate system utilized to plot the molecules being displayed);
(5) rotation capacity (allowing rotation in any of the three directions of the image being displayed);
(6) on/off control of the logical segments of the picture. For example, a line connecting the alpha carbons of the protein might be one logical segment; labels on same or all of the residues of the protein might be a second logical segment; a trace of the disulfide candidate might be a third segment; and Sulphur atoms of the adjacent residues of the protein might be a fourth logical segment. The user seldom wants to see all of these at once; rather the operator first becomes oriented by viewing the first two segments at low magnification. Then the labels are switched off and the disulfide trace is turned on. Once the general features of the disulfide candidate are seen, the operator zooms to higher magnification and turns on the segments which hold more detail;
(7) selection of atoms in the most detailed logical segment. Despite the power of modern graphics, the operator can be overwhelmed by too much detail at once. Thus the operator will pick one atom and ask to see all amino acids within some radius of that atom, typically six Angstroms, but other radii can be used. The user may also specify that certain amino acids will be included in addition to those that fall within the specified radius of the selected atom;
(8) changing of the colors of a various portion of the image being displayed so as to indicate to the viewer particular information using visual queuing.

As stated above, in the preferred embodiment of the present invention the application software is run on version 4.4 of the Vax/Vms operating system used in conjunction with CPU 102. The application programs were programmed using the FLECS (FORTRAN Language with Extended Control Sections) programming language written in 1974 by Terry Beyer of the University of Oregon, Eugene, Oreg. The FLECS is a FORTRAN preprocessor, which allows more logical programming. All of the code used in the current embodiment was developed in FLECS. It can be appreciated, however, that the present invention encompasses other operating systems and programming languages.

The macromolecules displayed on color display 120 of the computer-graphics display system 116 utilizes an extensively modified version of version 5.6 of FRODO. FRODO is a program for displaying and manipulating macromolecules. FRODO was written by T. A. Jones at Max Flanck Institute for Biochemistry, Munich, West Germany, for building or modeling in protein crystallography. FRODO version 5.6 was modified so as to be driven by command files; programs were then written to create the command files. It is utilized by the electronic stage 118 to display and manipulate images on the color display 120. Again, any suitable type of program can be used for displaying and manipulating the macromolecules, the coordinates of which are provided to the computer-graphics display system 116 by the CPU 102.

Design documentation and memos were written using PDL (Program Design Language) from Caine, Farber & Gordon of Pasadena, Calif. Again, any suitable type of program can be used for the design documents and memos.

FIG. 3 shows in block diagram form a preferred version of the hardware system of the present invention. Like numbers refer to like items of FIG. 2. Only the differences between the serial processor mode system of FIG. 2 and the improved system of FIG. 3 are discussed below.

The CPU 102' is the latest version of the Vax 11/780 from Digital Equipment Corporation. The latest processor from DEC in the VAX product family is approximately ten times faster than the version shown in the serial processor mode of FIG. 2.

Instead of the two Rm$\phi$5 disk drives 108 of FIG. 2, the embodiment of FIG. 3 utilizes five RA 81 disk drive units 110'. This is to upgrade the present system to more state of the art disk drive units, which provide greater storage capability and faster access.

Serial processor 106 is connected directly to the electronic stage 118, of the computer-graphics display system 116. The parallel interface in the embodiment of FIG. 3 replaces the serial interface approach of the serial processor mode of FIG. 2. This allows for faster interaction between CPU 102, and electronic stage 118' so as to provide faster data display to the expert operator.

Disposed in front of color display 120 is a stereo viewer 202. A suitable form for stereo viewer 202 is made by Terabit, Salt Lake City, Utah. Stereo viewer 202 would provide better 3-D perception to the expert operator than can be obtained presently through rotation of the molecule.

In addition, this embodiment replaces the FRODO macromolecule display programs with a program designed to show a series of related hypothetical molecules. This newer program performs the operations more quickly so that the related hypothetical molecules can be presented to the expert operator in a short enough time that makes examination less burdensome on the operator.

The program can be modified so as to cause the present invention to eliminate candidates in the third general step where the new disulfide bridge would obviously crowd retained atoms of the wild-type protein.

In addition, the third general step can be refined in several ways. For example, the model volumes of the atoms in the neighborhood of the new disulfide bridge could be calculated. Here the volume of an atom means the volume of space closer to that atom than to any other. Thus an atom in a loosely-packed region will appear to have a large volume. Atoms with large volumes can move more easily than atoms with small volumes. Thus a short contact between a new atom and a retained atom which has large volume is less damaging than a short contact with a retained atom of small volume. Using standard energy-minimization programs, one can eliminate most bond stretching, bond bending, bond torsion, and unfavorable non-bonded interactions. Calculation of the volumes of all atoms in the region will show whether a suitable geometry has been obtained. A geometric distribution of atoms in which each atom has the same volume as other atoms of the same type in natural proteins is more likely to correspond to a stabilized protein than one in which the atomic volumes depart widely from observed averages.

Another method which could be used to estimate the probable stabilizing influence of new disulfide bridges is molecular dynamics. Molecular dynamics could be used to determine whether atoms in the neighborhood of the new disulfide bridge can rearrange to accommodate the new crosslink. calculated. The November 1986 release of BPDB contained 512 reported disulfide bridges.

Those disulfide linkages which departed from average distances by more than 10% were considered suspicious. The data obtained from these structures may however still be useful, because all that is required is (1) that a disulfide bridge does, in fact, exist, and (2) the nature of the relationship between the two segments of main chain. Thus reported disulfide bridges with incorrect intersulfur distances are not simply rejected, rather attempts to impose correct internal geometry by small movements of the sulfur atoms (i.e., less than 0.2 Å) or very small movements of the beta carbons (less than 0.1 Å) are made.

Once disulfide bonds with unacceptable and unrepairable geometry are rejected, the program compares each reported disulfide with all others to eliminate geometric duplicates. For this purpose, two disulfide bonds are considered the same if ten of their atoms can be superimposed on the corresponding atoms with an RMS error less than 0.2 Å. Removal of duplicates reduced the original 512 reported disulfide bonds to 138 unique ones.

In order to further refine the three-dimensional configuration and intersulfur distances of the disulfide bridges, the pyramid formed from the nitrogen, alpha carbon, beta carbon and carbonyl carbon of the individual cysteines is examined. These 4 atoms have 12 coordinates, yet only 6 degrees of freedom. The pyramids formed from both of the cysteine residues are evaluated as follows. The 8 atoms (of the two pyramids) are translated until one pyramidal cluster set of 4 atoms has its center of mass at the origin. The constellation of 8 atoms is then rotated so that the plane formed by the nitrogen, carbonyl carbon, and the beta carbon is parallel to the X-Y plane. The alpha carbon is then positioned so as to have a positive Z coordinate (the other 3 atoms of the pyramid thus have the same negative Z coordinate). The pyramid is then rotated about the Z axis until the nitrogen atom has a zero Y coordinate. This defines the standard position for the cysteine residue. The coordinates of this group are shown in Table 1.

TABLE 1

| Standard N—Ca—Cb—C Pyramid | | | |
|---|---|---|---|
| | x | y | z |
| N (nitrogen) | +1.40047 | +0.00000 | −0.11897 |
| Ca (alpha C) | +0.01174 | +0.00259 | +0.35693 |
| Cb (beta C) | −0.70690 | +1.25305 | −0.11897 |
| C (carbonyl C) | −0.70531 | −1.25564 | −0.11897 |

For each different disulfide bond, an external record is written recording:

(1) the protein in which the disulfide occurs,
(2) the two amino acids involved,
(3) the length of the vector from the center of one pyramidal cluster to the other (spherical coordinate, r),
(4) the spherical polar angular coordinates phi and theta of the center of the second cluster,
(5) the three rotations needed to orient the second cluster about its center,
(6) the value of $CHI_3$, the S—S dihedral angle.

This list of different observed disulfide bridges is used each time sites for introduction of disulfide bonds are sought for a protein which is to be stabilized. The library need be updated only when one obtains new protein structures containing potentially novel disulfide bridges.

C. The Selection of Sites to Stabilize a Protein

1. The Process in General

The process for selecting sites to stabilize a protein is preferably conducted through the use of a computer. The algorithm followed by this program is composed of six different steps. The algorithm is depicted in FIG. 4. First, in the manner described above, a pyramid whose vertices correspond to the standard coordinates of an amino acid in the protein under study is prepared. This amino acid is designated by the letter "K" and initially (K=1) corresponds to the first amino acid of the protein molecule. A similar standard coordinate pyramid is produced for a second amino acid of the protein under investigation. This second amino acid is designated by the letter "L." Initially, amino acid "L" is one amino acid away from amino acid "K" (i.e., initially, L=K+1). Once the two coordinate pyramids have been prepared, the distance between them is calculated. The computer program then determines whether the calculated distance between the two pyramids is within the bounds of the disulfide linkages stored in the library data base. If the calculated distance is not within the bounds of the library, L is tested against N. If L equals N, then K is tested against N−1. If K is less than N−1, then K is set to K+1 and L is set to 1, and the process iterates.

If L was less than N, the L is increased by and the process iterates. If K=N−1 and L=N, then all points have been examined.

If the distance between two calculated pyramids is found to be within the bounds of the values present in the library, then an eight atom image is constructed from the N, C alpha, C beta, and C carbonyl of each of the two pyramids. The computer program then scans the library of known disulfide linkages to find that linkage with the lowest RMS error between the eight atoms of the target protein and the corresponding eight atoms from a library entry. The program then repeats its scan in order to identify a second best fit disulfide linkage, subject to the restriction that CHI3 for the second best fit must differ from CHI3 of the best fit by at least some preset amount, 20° in preferred embodiment. Both the best fit and second best fit are recorded and stored for future use. The computer program then picks a next pair of amino acids by the same method as that used if the distance between pyramids had not been in range.

In the above-described manner the program loops through all possible amino acid K or L. Location of a standard pyramid at amino acids K and L exploits the redundancy of the twelve coordinates which determine the 6 degrees of freedom. If either amino acid K or L is badly distorted, the computer program advises the user of this problem and the faulty amino acid is discarded.

As an example, the protein, staphylococcal nuclease which has 141 amino acids, contains 10,011 amino acid pairs. Of these, 387 were close enough to define a distance which was in the bounds of the disulfide linkages contained in the library.

Significantly, the pair of amino acids being evaluated is tested in both the direction L to K and the direction K to L. This is necessary because the geometries of cystines do not have a two-fold rotational symmetry about the midpoint of the S—S bond.

Once the RMS errors of the amino acid pair is determined relative to each disulfide bridge in the library, the list of RMS errors is scanned to find that entry which produced the smallest error. If this smallest error is below the preset threshold (for example, 0.40–0.55 Å, preferably 0.45 Å), an external record is written. The list of RMS errors is then searched for a second best fit subject to the condition that the dihedral angle CHI3 of the second-best fit must differ from the angle CHI3 by at least some minimal preset amount (i.e., 15–25 degrees). This second-best fit is recorded if its RMS error falls below the preset threshold value.

2. The Process in Detail

The process through which the novel computer program of the present invention identifies potential sites for disulfide bond crosslinking may be more fully explained through reference to FIG. 5.

Referring to FIG. 5, the DO-loops defined in lines 6000 and 6030 step through all possible pairs of amino acids K and L. Location of a standard N-Ca-Cb-C pyramid at amino acids K and L in lines 6010 and 6040 exploits the redundancy of the twelve coordinates which determine six degrees of freedom; this process is explained in further detail in FIG. 6 and in text below. If either amino acid K or L is badly distorted, the user is advised of the problem, but no further action is taken with the faulty amino acid (lines 6020 and 6050). At line 6060 the program calculates the distance between the two pyramids, as described in FIG. 7 and in the text below. The loop from line 6070 to line 6190 is entered only if the two pyramids are close enough together that a suitable fit is possible. In examining the protein staphylococcal nuclease which has 141 amino acids, 10,011 amino acid pairs were examined. Of these, 387 were close enough that the loop from 6070 to 6190 was entered. At line 6080 a loop over the different observed disulfide bridges is initiated. At line 6090 the current pair of amino acids is tested with amino acid K as the first and L as the second. At line 6100 the current pair is tested with L as the first and K as the second. This is necessary because the geometries of disulfide linkages do not have two-fold rotational symmetry about the midpoint of the S—S bond. The DO-loop begun on line 6080 ends on line 6110. On line 6120 the list of 2*(Number-of-different-observed-Cystines) RMS-errors is scanned to find the smallest error. If this smallest error is below the present threshold (0.45 A in preferred embodiment), and external record is written (line 6140). In line 6150, the list of RMS errors is searced for a second best fit subject to the condition that the dihedral angle CHI3 of the second-best fit must differ from the dihedral angle CHI3 of the best fit by at least some preset amount (20 degrees in preferred embodiment). In lines 6160 through 6180 this second-best fit leads to an external record if its RMS error falls below the preset threshold. The remainder of the procedure closes the various logical blocks.

The procedure LOCATE_STANDARD_PYRAMID_AT_AMINO_ACID_x is described in FIG. 6. In lines 7010 through 7030 glycines in the wild-type protein are augmented with a fictive beta carbon which can easily be defined from the locations of N, Ca, and C. In lines 7040 through 7044 the procedure tests to see that all four atoms, (N, Ca, Cb, and C) are present in the model. If atoms are absent, then lines 7050 through 7080 are not executed and the amino acid x=(either K or L) is eliminated from further consideration. If all atoms are present, then lines 7050 through 7080 are executed. In line 7060 the standard N-Ca-Cb-C pyramid is least-squares fit to the four atoms of the current amino acid x. This means that the coordinated of the standard pyramid can be translated or rotated as a group to minimize the distance between corresponding atoms. This was achieved with a public-domain set of subroutines called MOLFIT written by Dr. James Remington. MOLFIT returns the RMS_error; in line 7070 the RMS_error is compared to a preset threshold, 0.2 A in preferred embodiment. Lines 7080 and 7090 indicate closure of logical locks.

The procedure CALCULATE_DISTANCE_BETWEEN_PYRAMIDS is illustrated in FIG. 7. In line 8010 the coordinated of all four atoms in the K pyramid are summed and the sum divided by 4 to give a center-of-mass for the K pyramid. In line 8020 the center-of-mass of pyramid L is calculated. In line 8030 the separation is calculated as the standard Euclidian distance.

The procedure CALCULATE_RMS_ERROR_VS_pyr#1:pyr#2 is illustrated in FIG. 8. In line 9010, the four atoms from pyramid #1 (K or L) are made to correspond to the four atoms (nitrogen, alpha carbon, beta carbon and carbonyl carbon) of one half-cystine in the disulfide bridge. In line 9020, the four atoms from pyramid #2 (L or K) are made to correspond to the four atoms of the other half-cystine in the observed disulfide bridge. In line 9030 these two collections of eight atoms are rotated and translated as rigid bodies to obtain least squared error between corresponding atoms. The least-squared error is reported in line 9040.

D. The Elimination of Potential Candidates

The above-described computer program provides a list of potential disulfide linkages which may be used to connect two regions of a protein molecule in an effort to stabilize that molecule. If the group of potential linkages is small, it may be feasible for one to construct protein molecules which possess each of the identified disulfide bridges. If, however, the selected group of linkages is large, it may not be possible to produce an entire set of engineered protein molecules. In such a situation, it is desirable to rank the identified disulfide bridges and to eliminate candidates which are less likely to provide a stabilizing influence on the protein of interest.

1. Elimination of Candidates Based Upon Considerations of Steric Interactions The stable folding of proteins is dominated by the packing of hydrophobic groups against each other and away from the generally aqueous solvent. It is essential that the volume inside the protein be nearly filled and that polar or charged groups make appropriate interactions with each other or with the solvent molecules. In natural proteins, some water molecules are found inside the protein and form hydrogen bonds with oxygen or nitrogen atoms of the internal surface of the protein. Many carbon and sulfur atoms (and the hydrogen atoms covalently bound to these atoms) are found to be in van der Waals contact with other non-polar atoms. Proteins form such densely packed structures because a tightly compressed protein structure allows greater volume to the water and thus increases the entropy of the solvent. Hence, protein structure is not predominantly the result of the very weak attractive van der Waals forces between the protein atoms. In natural proteins, atoms are never closer than their van der Waals radii contact because of repulsive forces.

The simplest selection process for potential disulfide bridges would be to place all the atoms in the candidate structures and to then calculate the interatomic separations between the atoms of the disulfide bridge and all the retained atoms of the native protein. Candidates in which two atoms appear to be closer than permitted would be rejected. This very simple method is not used for two reasons:

(1) The recorded protein coordinates may contain errors.

(2) Protein structures are not static, and hence some steric hindrance may be permissible.

Thus, in order to eliminate less probable candidates on the basis of packing considerations, a more sophisticated analysis is required. A potential steric interference between the atoms is recorded only when the atoms are closer than their van der Waals radii by some preset amount (i.e., preferably 0.4-0.6 Å). Moreover, such contacts are divided into two classes which are separately evaluated. The first considered class are those in which the potentially interfering atoms are members of the main-chain of the protein. Contacts with main-chain atoms are more serious because the motion needed to relieve any steric interference might seriously disrupt the tertiary structure of the protein. In contrast, conflicts between hypothetical disulfide bridge atoms and atoms in other side chains might be easily relieved through rotations about side-chain bonds. Because of these considerations, the beta carbon is considered a main-chain atom because it is not moved by rotations about any side-chain bond.

Given the number of sites at which main-chain groups are correctly related for introduction of a new disulfide bridge, it is usually possible to find several of these sites for which there are no short contacts (i.e., steric interference) with either main-chain atoms or side-chain atoms.

A second consideration in evaluating possible disulfide bridges is to not lose favorable hydrophobic interactions. Thus, conversion of tryptophan, tyrosine, and phenylalanine residues to cysteine is probably unfavorable because this would create a large hole inside the protein. In contrast, conversion of leucine, isoleucine, or methionine into cysteine is only mildly unfavorable.

2. Elimination of Candidates Based Upon Considerations of Sequence Conservation A tenet of evolution is that the replication of genes is not error-free. Each error in copying a gene potentially alters the meaning of the encoded message. Because the genetic code has redundancies, many copying errors are silent and do not result in a change in the amino acid sequence encoded by the gene. For example, a mutation which changes a codon sequence of AAG into the codon sequence AAA would not effect the amino acid sequence of the encoded protein (which would in both cases be the amino acid lysine).

If a particular protein is produced in several different species, then, by comparing their amino acid sequences, it is possible to obtain insight into which amino acid residues appear to have been conserved (and thus probably essential) throughout evolutionary time. In evaluating potential positions for disulfide bridges, it is, therefore, desirable not to remove or alter any evolutionally conserved amino acid sequences. Thus, the number of potential candidate linkages may be reduced through a consideration of evolutionary protein change.

E. Recombinant DNA Manipulations

1. Production of Engineered Proteins

The primary amino acid sequence of a protein may be stored within the deoxyribonucleic acid (DNA) of a cell capable of producing that protein. Thus, by altering the DNA which encodes a particular protein, it is possible to change that protein's primary sequence. Although it is possible to change a protein's amino acid sequence either directly (as by incorporating additional cysteine residues by synthetic or semi-synthetic methods) or indirectly (as by altering the DNA or RNA sequence which encodes that protein, it is far more advantageous to alter the protein's amino acid sequence indirectly. Indirect means are preferred because (1) it is far easier to alter a DNA sequence than to alter a protein sequence, and (2) the capacity of DNA to self-replicate enables one to produce an inexhaustible supply of the desired protein molecule.

The process through which DNA is decoded to produce a protein molecule involves the synthesis of a ribonucleic acid (RNA) intermediary. The process through which RNA is produced is known as "transcription." The process through which the RNA molecule is decoded to produce a protein molecule is referred to as "translation." A description of these processes can be found in *The Structure and Action of Proteins* (Dickerson, R. E. et al., W. A. Benjamin, Inc., Calif. (1969)) and *Molecular Biology of the Gene* (Watson, J. D.; W. A. Benjamin, Inc., New York (1970)). The overall processes through which a DNA sequence is converted into a protein is often referred to as "gene expression." The expression of a DNA sequence requires that the sequence be "operably linked"to DNA sequences which contain transcriptional and translational regulatory information. An operable linkage is a linkage in which the regulatory DNA sequences and the sequences sought to be expressed are connected in such a way as to permit gene expression. The regulatory DNA sequences involved in gene expression are termed "promoters."

The term "promoter" as used herein refers to a region of regulatory DNA sequence which is recognized by a cell as a site adjacent to which to begin the initiation of the transcription of DNA into RNA. Examples of promoters from prokaryotic cells or from viruses which infect prokaryotic cells, include the *E. coli* recA, lac, and trp promoters (Shirakawa, M. et al., *Gene*, 28:127-132 (1984)) or the left promoter of bacteriophage lambda ($P_L$) (Devare, S. G., et al. *Cell*, 36:43-49 (1984)). Examples of promoters from eukaryotic cells or from viruses which infect such cells include the promoter of the mouse metallothionein I gene (Hamer, D., et al., *J. Mol. Appl. Gen.* 1:273-288 (1982)); the TK Promoter of Herpes virus (McKnight, S., *Cell* 31:355-365 (1982)); and the SV40 early promoter (Benoist, C. et al., *Nature*, 290:304-310 (1981)).

Thus, in order to produce a protein, a genetic sequence which encodes that protein is operably linked to a promoter region, and introduced into a suitable cell (such as *E. coli*, Bacilles, yeast, or mammalian cells). A DNA sequence may be introduced into a cell by any of several means: transduction, transformation, conjugation, or microinjection, although it is most preferable to use transformation (Botstein, D., et al., *The Molecular Biology of the Yeast Saccharomyces: Metabolism and Gene Expression*, Cold Spring Harbor, N.Y., 11B:607-636 (1982); Struhl, K., *Nature*, 305:391-397 (1983); Bollon, A. P., et al., *J. Clin. Hematol. Oncol.* 10:39-48 (1980); Wigler, M. et al., *Proc. Natl. Acad. Sci.* (U.S.A.), 76:1373-1376 (1979); Davis, R. W., et al., *A Manual for Genetic Engineering Advanced Bacterial Genetics*, Cold Spring Harbor, N.Y. (1980); Maniatis, T., *et al., Molecular Cloning A Laboratory Manual*, Cold Spring Harbor, N.Y., (1982); Miller, J. H., *Experiments in Molecular Genetics*, Cold Spring Harbor, N.Y. (1972)).

The genetic sequences which are capable of expressing the engineered proteins of the present invention are advantageously incorporated into self-replicating DNA plasmids. A plasmid is a covalently closed circular extrachromosomal nucleic acid molecule. In general, a plasmid contains two elements:

(1) An origin of replication sufficient to permit the propagation of the plasmid in a host cell; and (2) a selectable marker sequence, preferably a gene whose expression confers an antibiotic resistance to the host cell, sufficient to enable the maintenance of the plasmid within the host cell and to facilitate the manipulation and introduction of the plasmid into new host cells.

In summary, it is preferable to produce the engineered proteins of the present invention by manipulating the DNA sequences which encode those proteins. The manipulated DNA is then preferably incorporated into a plasmid molecule and introduced into a host cell which is capable of expressing such sequences, thereby producing the engineered protein molecule.

2. Production of Engineered Proteins by in vitro Mutagenesis of DNA

Techniques of *in vitro* mutagenesis involving M13 or its derivatives are disclosed by Kunkel, (*Proc. Natl. Acad. Sci. U.S.A.*, 82:488-492 (1985)), Nisbet, I. T., et al. (*Gene Anal. Tech.*, 2:23-29 (1985)), and Hines, J. C., et al., (*Gene*, 11:207-218 (1980)). In brief, the procedure entails the synthesis of a synthetic oligonucleotide having a desired and defined DNA sequence. M13, or one of its derivatives, is converted to its single strand form, and incubated in the presence of the synthetic oligonucleotide. Since the DNA of the oligonucleotide is controllably defined, it is possible to construct an oligonucleotide capable of pairing with a complementary DNA sequence present on the single stranded plasmid. Once base pairing has occurred between the oligonucleotide and the single stranded plasmid, it is possible to extend the oligonucleotide using DNA polymerase to create a double stranded DNA molecule which may then be sealed by DNA ligase. When this double stranded DNA molecule is introduced into a bacterial cell, semi-conservative DNA replication will result in the production of progeny molecules which now contain the DNA sequence of the oligonucleotide fragment (Messing, J., et al., *Nucl. Acid Res.*, 9:309 (1981)).

Thus, if one desires to introduce a cysteine residue into a specific site of a protein molecule one would design an oligonucleotide fragment which contains the codon for cysteine and then pursue the above described procedure. In order to introduce this mutation or exogenous DNA sequence into a particular region of a plasmid, it is necessary to surround the mutation or the exogenous DNA sequence with flanking DNA sequences which are complementary to the DNA sequence of the region whose mutagenesis is desired.

As an example, if a wild-type protein contains the amino acid sequence lysine-serine-leucine, then the corresponding DNA sequence might be AAA-TCT-CTT. If one desires to replace the serine with a cysteine residue, one would produce a DNA sequence such as AAA-TGT-CTT. The use of this oligonucleotide in the above-described in vitro mutagenesis method would result in the production of an altered gene which expresses a protein containing a cysteine residue in place of the original serine residue. In a similar manner, a cysteine residue can be incorporated into any position of any protein molecule.

Having now generally described this invention, the same will be better understood by reference to certain specific examples which are included herein for purposes of illustration only and are not intended to be limiting of the invention, unless specified.

EXAMPLE I

Production of Stabilized Serine Proteases

Serine proteases are proteolytic enzymes which have a serine residue at their active site. Many species of bacteria are known to secrete such serine proteases into the culture medium. Serine proteases can be inhibited by phenylmethanesulfonylfluoride and/or disopropylfluorophosphate. Subtilisin is a serine protease produced by Gram positive bacteria and fungi. The amino acid sequences of seven different subtilisins are known. These include five subtilisins (SBT) from Gram positive bacteria of the genus, Bacillus. The subtilisin produced by *Bacillus amylolicuifaciens* (hereinafter referred to as SBT BPN') was selected as a model protein and used to prepare an engineered, more stable protein. The wild type SBT BPN enzyme is discussed by Vasantha, et al. (*J. Bacteriol.*, 159:811-819 (1984). The three-dimensional structure of SBT BPN' has been determined to a resolution of 1.3 Å.

The number of potential pairs of disulfide linkage sites in a protein such as SBT BPN' is obtained from the following equation:

$$\text{Number of possible pairs} = \frac{N(N-1)}{2}$$

Hence, for a protein such as subtilisin, which has 275 amino acid residues (i.e., N=275) 37,675 different pairwise combinations are possible. Without the above-described computer method, it would be necessary to evaluate all of these possibilities experimentally.

Therefore, the above-described method for identifying potential sites which could be linked together with disulfide bonds was used in order to predict those linkages which would result in a more stable subtilisin protein. Before the computer method was applied, sites which included any of the residues Ser 221, Ser 125, His 64 or Asp 32 were discarded, since these residues are essential for subtilisin's catalytic activity. The results of the computer search for potential disulfide bond positions is shown in Table 2.

TABLE 2

Sites Selected for New Disulfide Bridges Using Geometry and Packing Based on the 1.3 A Crystal Structure of SBT BPN'

| Residues linked | Strain GX | RMS[a] error | Short M/C | Short S/C | CHI3 |
|---|---|---|---|---|---|
| G7:P201 | | 0.26 | 1 | 2 | 259 |
| Y21:S236 | | 0.45 | 0 | 0 | 274 |
| T22:S87 | 7159 | 0.39 | 0 | 0 | 244 |
| G23:A88 | | 0.44 | 4 | 0 | 270 |
| V26:A232 | | 0.45 | 0 | 1 | 259 |
| V26:L235 | 7157 | 0.42 | 0 | 0 | 275 |
| A29:A114 | | 0.36 | 0 | 2 | 273 |
| A29:M119 | | 0.44 | 0 | 0 | 149 |
| I31:G110 | | 0.17 | 1 | 2 | 268 |
| I35:A69 | | 0.28 | 3 | 0 | 84 |
| I35:A69 | | 0.38 | 6 | 0 | 269 |
| D36:H39 | | 0.18 | — | — | 244 |
| D41:G80 | | 0.22 | — | — | 84 |
| D41:G80 | | 0.26 | — | — | 269 |
| G47:P57 | | 0.36 | 3 | 3 | 89 |
| M50:N109 | 7168 | 0.30 | 0 | 0 | 275 |
| P57:K94 | | 0.35 | — | — | 71 |
| A85:A88 | | 0.40 | — | — | 244 |
| V93:G110 | | 0.38 | — | — | 268 |
| V95:I107 | | 0.43 | — | — | 101 |
| V95:G110 | | 0.42 | — | — | 88 |
| N123:A228 | | 0.29 | — | — | 78 |
| V150:A228 | | 0.36 | — | — | 93 |
| V150:A228 | | 0.45 | — | — | 226 |
| A153:V165 | | 0.38 | 1 | 0 | 252 |
| E156:T164 | | 0.29 | 0 | 1 | 89 |
| S163:G193 | | 0.44 | — | — | 65 |
| V165:K170 | | 0.41 | 0 | 2 | 145 |
| V165:S191 | | 0.23 | 3 | 0 | 101 |
| Y167:K170 | | 0.44 | — | — | 108 |
| V177:S224 | | 0.44 | — | — | 226 |
| A179:A223 | | 0.31 | — | — | 45 |
| A200:H226 | | 0.44 | — | — | 269 |
| Q206:A216 | 8307 | 0.27 | 0 | 0 | 88 |
| A230:V270 | | 0.35 | 0 | 1 | 90 |
| I234:A274 | | 0.41 | 0 | 0 | 274 |
| H238:W241 | | 0.36 | 0 | 0 | 244 |
| T253:A272 | | 0.42 | — | — | 89 |
| T253:A273 | 7140 | 0.29 | — | — | 93 |
| T253:A273 | " | 0.29 | — | — | 226 |

[a]Only RMS values of 0.45 and below were used in selecting these candidates.

In Table 2, the residues linked together are denoted using the single letter code for amino acids (see Table 3) and by the amino acid position number. Hence, the first linkage shown (G7:P201) denotes a potential linkage between cysteines which would replace the glycine which appears at position 7 of subtilisin and the proline which appears at position 201. The second column of Table 2 indicates whether a bacterial strain was constructed which expressed a protein having the indicated disulfide linkage. The third column is the RMS error for the best fit of the geometry of the candidate amino acid pair with that of any observed disulfide bond in the Brookhaven Protein Data Bank. The next two columns list the short contacts that occur between main or side-chain atoms (Short M/C; Short S/C) and thus provide an indication of the number of potential points of steric hindrance which are predicted to be present in the engineered protein. The final column of Table 2 provides the CHI3 angle of the bond in degrees.

TABLE 3

Letter Codes for the Naturally Occurring Amino Acids

| Alanine | ALA | A |
|---|---|---|
| Arginine | ARG | R |
| Aspartic acid | ASP | D |
| Asparagine | ASN | N |
| Cysteine | CYS | C |
| Glutamic acid | GLU | E |
| Glutamine | GLN | Q |
| Glycine | GLY | G |
| Histidine | HIS | H |
| Isoleucine | ILE | I |
| Lysine | LYS | K |
| Leucine | LEU | L |
| Methionine | MET | M |
| Phenylalanine | PHE | F |
| Proline | PRO | P |
| Serine | SER | S |
| Threonine | THR. | T |
| Tryptophan | TRP | W |
| Tyrosine | TYR | Y |
| Valine | VAL | V |

EXAMPLE II

Elimination of Selected Candidates on the Basis of Packing and Sequence Conservation Since the subtilisins from several Bacillus strains have been purified and sequenced, it is possible to compare these sequences and thereby identify conserved amino acid residues. In performing this comparison, the following references were employed: SBT BPN' (Vasantha et al., *J. Bacteriol.* 159:811-819 (1984)); SBT Carlsberg (Jacobs et al., *Nucleic Acid Res.* 13:8913-8926 (1985)); SBT DY (Nedov et al., *Biol. Chem.* 366:421-430 (1985)); SBT amylosacchariticus (Kurihara et al., *J. Biol. Chem.* 247:5619-5631 (1972)); and Mesenticopeptidase (Svendsen et al., *FEBS Lett.* 196:228-232 (1986)).

The amino acid sequence of the subtilisin thermitase from *Thermoactinomyces vulgaris* is also known (Meloun et al., *FEBS Lett.* 183:195-200 (1985)). The amino acid sequences from two fungal serine proteases are also partially known: proteinase K (Jany et al., *Biol. Chem. Hopoe-Seyler* 366:485-492 (1985)) and thermomycolase (Gaucher et al., *Methods Enzymol.* 45:415-433 (1976)).

These enzymes have been shown to be related to subtilisin BPN', not only through their primary sequence and enzymological properties, but also by comparison of x-ray crystallographic data (McPhalen et al., *FEBS Lett.* 188:55-58 (1985) and Pahler et al., *EMBO J.* 3:1311-1314 (1984)). A Comparison of subtilisin amino acid sequences is shown in Table 4.

TABLE 4

| PROTEASE RESIDUE | Subtilisin Sequences | | | | | |
|---|---|---|---|---|---|---|
| | 1 | 2 | 3 | 4 | 5 | 6 |
| −7 | — | — | — | — | — | TYR |
| −6 | — | — | — | — | — | THR |
| −5 | — | — | — | — | — | PRO |
| −4 | — | — | — | — | — | ASN |
| −3 | — | — | — | — | — | ASP |
| −2 | — | — | — | — | — | PRO |
| −1 | — | — | — | — | — | TYR |
| 1 | ALA | ALA | ALA | ALA | ALA | PHE |
| 2 | GLN | GLN | GLN | GLN | GLN | SER |
| 3 | ser | ser | ser | thr | thr | ser |
| 4 | VAL | VAL | VAL | VAL | VAL | ARG |
| 5 | PRO | PRO | PRO | PRO | PRO | GLN |
| 6 | TYR | TYR | TYR | TYR | TYR | TRP |
| 7 | GLY | GLY | GLY | GLY | GLY | GLY |
| 8 | val | ile | ile | ile | ile | pro |
| 9 | ser | ser | ser | pro | pro | gln |
| 10 | gln | gln | gln | leu | leu | lys |
| 11 | ILE | ILE | ILE | ILE | ILE | ILE |
| 12 | LYS | LYS | LYS | LYS | LYS | GLN |
| 13 | ALA | ALA | ALA | ALA | ALA | ALA |
| 14 | pro | pro | pro | asp | asp | pro |
| 15 | ala | ala | ala | lys | lys | gln |
| 16 | leu | leu | leu | val | val | ala |
| 17 | his | his | his | gln | gln | trp |
| 18 | ser | ser | ser | ala | ala | asp |
| 19 | GLN | GLN | GLN | GLN | GLN | ILE |
| 20 | GLY | GLY | GLY | GLY | GLY | ALA |
| 21 | tyr | tyr | tyr | phe | tyr | glu |
| 22 | thr | thr | thr | lys | lys | — |
| 23 | GLY | GLY | GLY | GLY | GLY | GLY |
| 24 | ser | ser | ser | ala | ala | ser |
| 25 | ASN | ASN | ASN | ASN | ASN | GLY |
| 26 | VAL | VAL | VAL | VAL | VAL | ALA |
| 27 | LYS | LYS | LYS | LYS | LYS | LYS |
| 28 | VAL | VAL | VAL | VAL | VAL | ILE |
| 29 | ala | ala | ala | ala | gly | ala |
| 30 | val | val | val | val | ile | ile |
| 31 | ile | ile | ile | leu | ile | val |
| 32 | ASP | ASP | ASP | ASP | ASP | ASP |
| 33 | ser | ser | ser | thr | thr | thr |
| 34 | GLY | GLY | GLY | GLY | GLY | GLY |
| 35 | ILE | ILE | ILE | ILE | ILE | VAL |
| 36 | asp | asp | asp | gln | ala | gln |
| 37 | ser | ser | ser | ala | ala | ser |
| 38 | SER | SER | SER | SER | SER | ASN |
| 39 | HIS | HIS | HIS | HIS | HIS | HIS |

TABLE 4-continued

| PROTEASE RESIDUE | Subtilisin Sequences | | | | | |
|---|---|---|---|---|---|---|
| | 1 | 2 | 3 | 4 | 5 | 6 |
| 40 | pro | pro | pro | pro | thr | pro |
| 41 | ASP | ASP | ASP | ASP | ASP | ASP |
| 42 | LEU | LEU | LEU | LEU | LEU | LEU |
| 43 | lys | asn | asn | asn | lys | ala |
| 44 | VAL | VAL | VAL | VAL | VAL | GLY |
| 45 | ala | arg | arg | val | val | lys |
| 46 | GLY | GLY | GLY | GLY | GLY | VAL |
| 47 | GLY | GLY | GLY | GLY | GLY | VAL |
| 48 | ALA | ALA | ALA | ALA | ALA | GLY |
| 49 | SER | SER | SER | SER | SER | GLY |
| 50 | met | phe | phe | phe | phe | trp |
| 51 | VAL | VAL | VAL | VAL | VAL | ASP |
| 52 | pro | pro | pro | ala | ser | phe |
| 53 | ser | ser | ser | gly | gly | val |
| 54 | GLU | GLU | GLU | GLU | GLU | GLU |
| 55 | thr | thr | thr | ala | ser | gln |
| 56 | asn | asn | asn | — | — | asp |
| 57 | pro | pro | pro | tyr | tyr | ser |
| 58 | phe | tyr | tyr | asn | asn | thr |
| 59 | gln | gln | gln | thr | thr | pro |
| 60 | ASP | ASP | ASP | ASP | ASP | GLN |
| 61 | asn | gly | gly | gly | gly | gly |
| 62 | asn | ser | ser | asn | asn | asn |
| 63 | ser | ser | ser | gly | gly | gly |
| 64 | HIS | HIS | HIS | HIS | HIS | HIS |
| 65 | GLY | GLY | GLY | GLY | GLY | GLY |
| 66 | THR | THR | THR | THR | THR | THR |
| 67 | HIS | HIS | HIS | HIS | HIS | HIS |
| 68 | VAL | VAL | VAL | VAL | VAL | CYS |
| 69 | ALA | ALA | ALA | ALA | ALA | ALA |
| 70 | GLY | GLY | GLY | GLY | GLY | GLY |
| 71 | THR | THR | THR | THR | THR | ILE |
| 72 | val | ile | ile | val | val | ala |
| 73 | ALA | ALA | ALA | ALA | ALA | ALA |
| 74 | ALA | ALA | ALA | ALA | ALA | ALA |
| 75 | LEU | LEU | LEU | LEU | LEU | VAL |
| 75a | — | — | — | — | — | THR |
| 76 | asn | asn | asn | asp | asp | asn |
| 77 | ASN | ASN | ASN | ASN | ASN | ASN |
| 78 | ser | ser | ser | thr | thr | ser |
| 79 | ile | ile | ile | thr | thr | thr |
| 80 | GLY | GLY | GLY | GLY | GLY | GLY |
| 81 | VAL | VAL | VAL | VAL | VAL | ILE |
| 82 | LEU | LEU | LEU | LEU | LEU | ALA |
| 83 | GLY | GLY | GLY | GLY | GLY | GLY |
| 84 | VAL | VAL | VAL | VAL | VAL | THR |
| 85 | ALA | ALA | ALA | ALA | ALA | ALA |
| 86 | PRO | PRO | PRO | PRO | PRO | PRO |
| 87 | ser | ser | ser | ser | asn | lys |
| 88 | ala | ala | ser | val | val | ala |
| 89 | ser | ser | ala | ser | ser | ser |
| 90 | LEU | LEU | LEU | LEU | LEU | ILE |
| 91 | TYR | TYR | TYR | TYR | TYR | LEU |
| 92 | ALA | ALA | ALA | ALA | ALA | ALA |
| 93 | val | val | val | val | ile | val |
| 94 | LYS | LYS | LYS | LYS | LYS | ARG |
| 95 | VAL | VAL | VAL | VAL | VAL | VAL |
| 96 | LEU | LEU | LEU | LEU | LEU | LEU |
| 97 | gly | asp | asp | asn | asn | asp |
| 98 | ala | ser | ser | ser | ser | asn |
| 99 | asp | thr | thr | ser | ser | ser |
| 100 | GLY | GLY | GLY | GLY | GLY | GLY |
| 101 | SER | SER | SER | SER | SER | SER |
| 102 | GLY | GLY | GLY | GLY | GLY | GLY |
| 103 | gln | gln | gln | thr | thr | thr |
| 104 | TYR | TYR | TYR | TYR | TYR | TRP |
| 105 | SER | SER | SER | SER | SER | THR |
| 106 | trp | trp | trp | gly | ala | ala |
| 107 | ILE | ILE | ILE | ILE | ILE | VAL |
| 108 | ile | ile | ile | val | val | ala |
| 109 | asn | asn | asn | ser | ser | asn |
| 110 | GLY | GLY | GLY | GLY | GLY | GLY |

TABLE 4-continued

Subtilisin Sequences

| PROTEASE RESIDUE | 1 | 2 | 3 | 4 | 5 | 6 |
|---|---|---|---|---|---|---|
| 111 | ILE | ILE | ILE | ILE | ILE | ILE |
| 112 | GLU | GLU | GLU | GLU | GLU | THR |
| 113 | TRP | TRP | TRP | TRP | TRP | TYR |
| 114 | ALA | ALA | ALA | ALA | ALA | ALA |
| 115 | ile | ile | ile | thr | thr | ala |
| 116 | ala | ser | ser | thr | gln | asp |
| 117 | ASN | ASN | ASN | ASN | ASN | GLN |
| 118 | asn | asn | asn | gly | gly | gly |
| 119 | met | met | met | met | leu | ala |
| 120 | ASP | ASP | ASP | ASP | ASP | LYS |
| 121 | VAL | VAL | VAL | VAL | VAL | VAL |
| 122 | ILE | ILE | ILE | ILE | ILE | ILE |
| 123 | ASN | ASN | ASN | ASN | ASN | SER |
| 124 | MET | MET | MET | MET | MET | LEU |
| 125 | SER | SER | SER | SER | SER | SER |
| 126 | LEU | LEU | LEU | LEU | LEU | LEU |
| 127 | GLY | GLY | GLY | GLY | GLY | GLY |
| 128 | GLY | GLY | GLY | GLY | GLY | GLY |
| 129 | PRO | PRO | PRO | PRO | PRO | THR |
| 130 | ser | ser | thr | ser | ser | val |
| 131 | GLY | GLY | GLY | GLY | GLY | GLY |
| 132 | SER | SER | SER | SER | SER | ASN |
| 133 | ala | thr | thr | thr | thr | ser |
| 134 | ALA | ALA | ALA | ALA | ALA | GLY |
| 135 | leu | leu | leu | met | leu | leu |
| 136 | LYS | LYS | LYS | LYS | LYS | GLN |
| 137 | ala | thr | thr | gln | gln | gln |
| 138 | ala | val | val | ala | ala | ala |
| 139 | VAL | VAL | VAL | VAL | VAL | VAL |
| 140 | ASP | ASP | ASP | ASP | ASP | ASN |
| 141 | lys | lys | lys | asn | lys | tyr |
| 142 | ALA | ALA | ALA | ALA | ALA | ALA |
| 143 | val | val | val | tyr | tyr | trp |
| 144 | ala | ser | ser | ala | ala | asn |
| 145 | ser | ser | ser | arg | ser | lys |
| 146 | GLY | GLY | GLY | GLY | GLY | GLY |
| 147 | val | ile | ile | val | ile | ser |
| 148 | VAL | VAL | VAL | VAL | VAL | VAL |
| 149 | VAL | VAL | VAL | VAL | VAL | VAL |
| 150 | val | ala | ala | val | val | val |
| 151 | ALA | ALA | ALA | ALA | ALA | ALA |
| 152 | ALA | ALA | ALA | ALA | ALA | ALA |
| 153 | ALA | ALA | ALA | ALA | ALA | ALA |
| 154 | GLY | GLY | GLY | GLY | GLY | GLY |
| 155 | ASN | ASN | ASN | ASN | ASN | ASN |
| 156 | glu | glu | glu | ser | ser | ala |
| 157 | GLY | GLY | GLY | GLY | GLY | GLY |
| 158 | thr | ser | ser | ser | ser | asn |
| 159 | SER | SER | SER | SER | SER | THR |
| 160 | GLY | GLY | GLY | GLY | GLY | ALA |
| 161 | ser | ser | ser | asn | ser | pro |
| 162 | ser | ser | thr | thr | gln | asn |
| 163 | ser | ser | ser | asn | asn | — |
| 164 | THR | THR | THR | THR | THR | — |
| 165 | val | val | val | ile | ile | — |
| 166 | GLY | GLY | GLY | GLY | GLY | — |
| 167 | TYR | TYR | TYR | TYR | TYR | TYR |
| 168 | PRO | PRO | PRO | PRO | PRO | PRO |
| 169 | gly | ala | ala | ala | ala | ala |
| 170 | LYS | LYS | LYS | LYS | LYS | TYR |
| 171 | TYR | TYR | TYR | TYR | TYR | TYR |
| 172 | pro | pro | pro | asp | asp | ser |
| 173 | SER | SER | SER | SER | SER | ASN |
| 174 | val | thr | thr | val | val | ala |
| 175 | ILE | ILE | ILE | ILE | ILE | ILE |
| 176 | ALA | ALA | ALA | ALA | ALA | ALA |
| 177 | VAL | VAL | VAL | VAL | VAL | VAL |
| 178 | GLY | GLY | GLY | GLY | GLY | ALA |
| 179 | ALA | ALA | ALA | ALA | ALA | SER |
| 180 | VAL | VAL | VAL | VAL | VAL | THR |
| 181 | asp | asn | asn | asp | asp | asp |
| 182 | SER | SER | SER | SER | SER | GLN |
| 183 | ser | ser | ala | asn | asn | asn |
| 184 | asn | asn | asn | ser | lys | asp |
| 185 | gln | gln | gln | asn | asn | asn |
| 186 | ARG | ARG | ARG | ARG | ARG | LYS |
| 187 | ALA | ALA | ALA | ALA | ALA | SER |
| 188 | SER | SER | SER | SER | SER | SER |
| 189 | PHE | PHE | PHE | PHE | PHE | PHE |
| 190 | SER | SER | SER | SER | SER | SER |
| 191 | SER | SER | SER | SER | SER | THR |
| 192 | val | ala | ala | val | val | tyr |
| 193 | GLY | GLY | GLY | GLY | GLY | GLY |
| 194 | pro | ser | ser | ala | ala | ser |
| 195 | GLU | GLU | GLU | GLU | GLU | VAL |
| 196 | LEU | LEU | LEU | LEU | LEU | VAL |
| 197 | asp | asp | asp | glu | glu | asp |
| 198 | VAL | VAL | VAL | VAL | VAL | VAL |
| 199 | MET | MET | MET | MET | MET | ALA |
| 200 | ALA | ALA | ALA | ALA | ALA | ALA |
| 201 | PRO | PRO | PRO | PRO | PRO | PRO |
| 202 | GLY | GLY | GLY | GLY | GLY | GLY |
| 203 | val | val | val | ala | val | ser |
| 204 | ser | ser | ser | gly | ser | trp |
| 205 | ile | ile | ile | val | val | ile |
| 206 | gln | gln | gln | tyr | tyr | tyr |
| 207 | SER | SER | SER | SER | SER | SER |
| 208 | THR | THR | THR | THR | THR | THR |
| 209 | leu | leu | leu | tyr | tyr | tyr |
| 210 | PRO | PRO | PRO | PRO | PRO | PRO |
| 211 | gly | gly | gly | thr | ser | thr |
| 212 | asn | gly | gly | ser | asn | ser |
| 213 | lys | thr | thr | thr | thr | thr |
| 214 | TYR | TYR | TYR | TYR | TYR | TYR |
| 215 | gly | gly | gly | ala | thr | ala |
| 216 | ala | ala | ala | thr | ser | ser |
| 217 | tyr | tyr | tyr | leu | leu | leu |
| 218 | ASN | ASN | ASN | ASN | ASN | SER |
| 219 | GLY | GLY | GLY | GLY | GLY | GLY |
| 220 | THR | THR | THR | THR | THR | THR |
| 221 | SER | SER | SER | SER | SER | SER |
| 222 | MET | MET | MET | MET | MET | MET |
| 223 | ALA | ALA | ALA | ALA | ALA | ALA |
| 224 | ser | thr | thr | ser | ser | thr |
| 225 | PRO | PRO | PRO | PRO | PRO | PRO |
| 226 | HIS | HIS | HIS | HIS | HIS | HIS |
| 227 | VAL | VAL | VAL | VAL | VAL | VAL |
| 228 | ALA | ALA | ALA | ALA | ALA | ALA |
| 229 | GLY | GLY | GLY | GLY | GLY | GLY |
| 230 | ALA | ALA | ALA | ALA | ALA | VAL |
| 231 | ALA | ALA | ALA | ALA | ALA | ALA |
| 232 | ALA | ALA | ALA | ALA | ALA | GLY |
| 233 | LEU | LEU | LEU | LEU | LEU | LEU |
| 234 | ILE | ILE | ILE | ILE | ILE | LEU |
| 235 | LEU | LEU | LEU | LEU | LEU | ALA |
| 236 | SER | SER | SER | SER | SER | SER |
| 237 | LYS | LYS | LYS | LYS | LYS | GLN |
| 238 | his | his | his | his | tyr | — |
| 239 | PRO | PRO | PRO | PRO | PRO | — |
| 240 | asn | thr | thr | asn | thr | gly |
| 241 | trp | trp | trp | leu | leu | arg |
| 242 | thr | thr | thr | ser | ser | ser |
| 243 | asn | asn | asn | ala | ala | ala |
| 244 | thr | ala | ala | ser | ser | ser |
| 245 | GLN | GLN | GLN | GLN | GLN | ASN |
| 246 | VAL | VAL | VAL | VAL | VAL | ILE |
| 247 | ARG | ARG | ARG | ARG | ARG | ARG |
| 248 | ser | asp | asp | asn | asn | ala |
| 249 | ser | arg | arg | arg | arg | ala |
| 250 | LEU | LEU | LEU | LEU | LEU | ILE |
| 251 | glu | glu | glu | ser | ser | glu |
| 252 | asn | ser | ser | ser | ser | asn |
| 253 | THR | THR | THR | THR | THR | THR |
| 254 | thr | ala | ala | ala | ala | ala |

TABLE 4-continued

| | Subtilisin Sequences | | | | | |
|---|---|---|---|---|---|---|
| PROTEASE RESIDUE | 1 | 2 | 3 | 4 | 5 | 6 |
| 255 | THR | THR | THR | THR | THR | ASP |
| 256 | lys | tyr | tyr | tyr | asn | lys |
| 257 | LEU | LEU | LEU | LEU | LEU | ILE |
| 257a | — | — | — | — | — | SER |
| 258 | GLY | GLY | GLY | GLY | GLY | GLY |
| 259 | asp | asp | ser | ser | asp | thr |
| 260 | SER | SER | SER | SER | SER | GLY |
| 261 | PHE | PHE | PHE | PHE | PHE | THR |
| 262 | TYR | TYR | TYR | TYR | TYR | TYR |
| 263 | TYR | TYR | TYR | TYR | TYR | TRP |
| 264 | GLY | GLY | GLY | GLY | GLY | ALA |
| 265 | LYS | LYS | LYS | LYS | LYS | LYS |
| 266 | GLY | GLY | GLY | GLY | GLY | GLY |
| 267 | LEU | LEU | LEU | LEU | LEU | ARG |
| 268 | ILE | ILE | ILE | ILE | ILE | VAL |
| 269 | ASN | ASN | ASN | ASN | ASN | ASN |
| 270 | VAL | VAL | VAL | VAL | VAL | ALA |
| 271 | gln | gln | gln | glu | glu | tyr |
| 272 | ALA | ALA | ALA | ALA | ALA | LYS |
| 273 | ALA | ALA | ALA | ALA | ALA | ALA |
| 274 | ALA | ALA | ALA | ALA | ALA | VAL |
| 275 | GLN | GLN | GLN | GLN | GLN | GLN |
| 276 | — | — | — | — | — | TYR |

Key:
1 Subtilisin BPN'
2 Subtilisin Amylosacchariticus
3 Mesenticopeptidase
4 Subtilisin Carlsberg
5 Subtilisin DY
6 Thermitase
Sequences 1-5 are from bacilli.
XXX Conserved in all sequences - (capitalized and underlined)
XXX Conserved in Bacillus - (capitalized)
xxx Varies within Bacillus - (lower case)

Comparing all sequences, there are 91 completely conserved residues while 194 of the residues vary. The Bacillus sequences are more closely related with 171 of 275 being conserved. The 40 potential disulfide linkage sites identified by the computer program were then analyzed to determine whether any of these linkages would involve the alteration of a conserved amino acid residue. Those residue linkages which did not result in the alteration of a conserved amino acid are shown in Table 5.

TABLE 5

Sites Selected for New Disulfide Bridges Using Geometry, Packing, & Homology

| Residues linked | Strain GX | RMS[b] error | Short M/C | Short S/C | CHI$_3$ |
|---|---|---|---|---|---|
| T22:S87 | 7159 | 0.39 | 0 | 0 | 244 |
| V26:L235 | 7157 | 0.42 | 0 | 0 | 275 |
| G47:P57 | | 0.36 | 3 | 3 | 89 |
| M50:N109 | 7168 | 0.30 | 0 | 0 | 275 |
| E156:T164 | | 0.29 | 0 | 1 | 89 |
| V165:K170 | | 0.41 | 0 | 2 | 145 |
| V165:S191 | | 0.23 | 3 | 0 | 101 |
| Q206:A216 | 8307 | 0.27 | 0 | 0 | 88 |
| A230:V270 | | 0.35 | 0 | 1 | 90 |
| I234:A274 | | 0.41 | 0 | 0 | 274 |
| H238:W241 | | 0.36 | 0 | 0 | 244 |

[b]Only RMS values of 0.45 Å and below were used in selecting these candidates.

As seen in Table 5, 11 linkages were identified as possible candidates for introduced disulfide bonds that would increase the stability of SBT BPN'. The 11 linkages were then examined to identify those linkages having the least RMS error and the fewest steric hindrances (short contact main-chain and side-chain interactions). Six out of these eleven are shown to have no short contacts with main-chain and side-chain atoms.

Four of these, T22:S87, Y26:L235, M50:N109, and chain Q206:A216 were selected for oligonucleotide-directed mutagenesis, and the variant proteins containing these selected disulfide bridges were called subtilisin 7159, 7157, 7168, and 8307, respectively.

EXAMPLE III

Production of Engineered Proteins

Using the technique of oligonucleotide-directed in vitro mutagenesis, described above, strain GX7157 was constructed. In this strain, the SBT BPN' protein contains cysteine residues at position 26 (replacing valine) and at position 235 (replacing leucine). Strain GX7157 was found to be capable of producing and secreting subtilisin. The disulfide bond may have formed, but the resultant protein was decidedly less stable than wild-type. It was observed that the single substitution of a cysteine for the lysine residue at position 235 was mildly destabilizing. In contrast, the engineered protein which possessed a cysteine instead of a valine at position 26 was approximately as stable as the wild-type protein.

A second mutant strain was constructed which contained cysteines at position 50 (replacing methionine) and position 109 (replacing asparagine). This mutant strain was designated GX7168. Subtilisin was produced in this strain and secreted, however, the engineering protein was decidedly less stable than wild-type.

A third mutant strain was constructed in which the threonine at position 22 and the serine at position 87 were replaced by cysteines. This mutant was designated GX7159. The subtilisin secreted by this strain was found to contain the desired disulfide bond. This engineered protein was decidedly more stable than wild-type subtilisin.

In 10 mM calcium chloride, the rate for thermal inactivation of subtilisin 7159 (i.e., produced from mutant strain GX7159) is 1.1 times slower than wild-type subtilisin BPN' at 65° C. In 1 mM EDTA, the rate of thermal inactivation at 45° C. for subtilisin 7159 is 1.5 to 2.0 times slower than that for wild-type subtilisin BPN'. It is well known that subtilisin is stabilized by free calcium ions. Many preparations for washing clothes contain agents to sequester calcium because free calcium interferes with the action of detergents. Thus the improved stability of subtilisin 7159 in a calcium-free environment (i.e., an environment containing EDTA) is especially useful.

In addition, subtilisin 7159 was melted in a differential scanning calorimeter. In 10 mM calcium chloride, subtilisin 7159 melted 0.5° C. above the melting temperature of wild-type subtilisin. In 10 mM EDTA, subtilisin 7159 melted 3.1° C. above the melting temperature of wild-type subtilisin. Thus, subtilisin 7159 was substantially more thermodynamically stable than the wild-type protein.

A mutant was constructed which contained cysteine residues at position 206 (replacing glutamine) and at position 216 (replacing alanine). This mutant was designated GX8307. The subtilisin secreted by this mutant was found to contain the desired disulfide bond. The subtilisin produced by GX8307 (termed subtilisin 8307) was decidedly more stable than wild-type subtilisin.

In 10 mM calcium chloride, the rate for thermal inactivation at 65° C. for subtilisin 8307 is 1.1 times slower than that of wild-type subtilisin BPN'. In 1 nM EDTA, the rate of thermal inactivation at 45° C. for subtilisin 8307 is also 1.5 to 2.0 times slower than wild-type subtilisin BPN'. In addition, subtilisin 8307 was melted in a differential scanning calorimeter. In 10 nM EDTA, subtilisin 8307 melted about 3.0° C. above the melting temperature of wild-type subtilisin. Thus, subtilisin 8307 was substantially more stable than the wild-type protein. Since, as indicated above, subtilisin is stabilized by free calcium ions, the improved stability of subtilisin 8307 in a calcium-free environment is again especially useful for an enzyme to be introduced into detergents for washing clothes.

Using oligonucleotide-directed mutagenesis, the disulfide bond of subtilisin 7159 (cysteines at positions 22 and 87) was combined in the same subtilisin molecule with a stabilizing mutation (asparagine 218 to serine) identified by random mutagenesis. (The 218 random mutation is described in co-pending, commonly assigned PCT Patent Application 87/00348.) This new subtilisin molecule (subtilisin 7181), which was secreted by strain GX7181, contained the desired disulfide bond and was decidedly more stable than wild-type.

Subtilisin 7181 was crystallized isomorphously to wild-type subtilisin. Using these crystals, x-ray data was collected to a resolution of 1.8 Å. The phases of wild-type subtilisin were used to initiate Hendrickson-Konnert refinement (Hendrickson, W. H. and Konnert, J. H. (1980) In: *Computing in Crystallography*, (Diamond, R., Ranseshan, S. and Venkatesan, K., eds.), pp. 13.01–13.23, Indian Institute of Science, Bangalore) which was continued until the crystallographic R index was 14.5. The disulfide bridge was found to be in the predicted conformation.

In 10 mM calcium chloride, the rate of thermal inactivation of subtilisin 7181 is 4.0 times slower than that of wild-type subtilisin BPN' at 65° C. In 1 mM EDTA, the rate of thermal inactivation at 45° C. for subtilisin produced by GX7181 is approximately 5.2 times slower than that of wild-type subtilisin BPN'. In addition, subtilisin 7181 was melted in a differential scanning calorimeter. In 10 mM EDTA, subtilisin 7181 melted 7.5° C. above the melting temperature of wild-type subtilisin. Thus, subtilisin 7181 was substantially more stable than the wild-type protein. Thus, the subtilisin produced by GX7181, which exhibits improved stability in a calcium-free environment, is especially useful in preparations which contain detergents.

Also using oligonucleotide-directed mutagenesis, the disulfide bond of subtilisin 7159 (cysteines at positions 22 and 87) was combined with the disulfide bond of subtilisin 8307 (cysteines at positions 206 and 216) to create subtilisin 8310. Subtilisin 8310, produced by strain GX8310, was found to be secreted and to contain both of the desired disulfide bonds. Subtilisin 8310 was melted in a differential scanning calorimeter. In 10 mM EDTA, subtilisin 8310 melted about 5.5° C. above the melting temperature of wild-type subtilisin. Thus, subtilisin 8310 was substantially more stable than the wild-type protein.

The reasons for the failure of the disulfide linkages contained in subtilisin 7157 and 7168 to stabilize these proteins is unknown at the present time. Residues Val 26 and Leu 235 which are changed to cysteines in subtilisin 7157 are less variable than many of the other residues listed in Table 5, especially when compared with those involved in the disulfide linkages of 22/87 and 206/216. Residues 26 and 235 are absolutely conserved within the Bacillus genus, and differ only in the thermitase sequence from Thermoactinomyces. These residues are decidedly more hydrophobic than those comprising the disulfide linkages in subtilisin 7159 and 8307. It is believed that one loses more stability from removing hydrophobic residues from the interior of the protein than one can gain from the effect of a crosslink on the entropy of the unfolded state. The 50/109 linkage may also suffer from this same problem since only very hydrophobic groups (Met, Phe, and Trp) are found at this position.

Additional considerations such as these could lead to an improvement in the probability for selecting stabilizing disulfide linkages. Nonetheless, even without any further modifications of this method, its success rate for predicting candidate sites on proteins for the introduction of disulfide linkages is two out of four or 50%. No other known method for selecting disulfide linkages approaches this level of success. The method of Wetzel (European Patent Appln. No. 155,832) has no success in selecting sites when more than one cysteine needs to be changed.

As an indication of the necessity for the various steps and rules defined in this present invention, and also as an insight to how they evolved and were formulated, it becomes instructive to review examples of engineered disulfide linkages that failed to stabilize subtilisin BPN'. A list of unsuccessful attempts to engineer disulfide linkages in subtilisin by means outside the present embodiment of the current invention is given in Table 6.

TABLE 6

| | Geometry and Homology Parameters for Disulfide Bridge Sites that Failed to Stabilize Subtilisin BPN' | | | | | | |
|---|---|---|---|---|---|---|---|
| Residues linked | Strain GX | RMS error | Short M/C | Short S/C | CHI$_3$ | Sequence[c] Homology | Effect on Stability |
| A1:S78 | 7127 | 0.48 | 0 | 0 | 272 | NC | unchanged |
| A1:S78 | " | 0.54 | 0 | 0 | 252 | " | " |
| S24:S87 | 7123 | 0.51 | 2 | 1 | 270 | NC | unchanged |
| K27:S89 | 7136 | 0.71 | 1 | 1 | 239 | K27 AC | unchanged |
| A85:A232 | 7122 | 0.73 | — | — | 260 | A85 AC | decreased |
| A85:A232 | " | 0.73 | — | — | 83 | " | " |
| I122:V147 | 7115 | 0.83 | — | — | 149 | I122 AC | decreased |
| S249:A273 | 7124 | 0.67 | — | — | 294 | A273 AC | decreased |
| T253:A273 | 7140 | 0.29 | — | — | 93 | A273 & T253 AC | decreased |
| T253:A273 | " | 0.29 | — | — | 226 | " | " |

Of the examples shown in Table 6, all except the 253/273 linkage have RMS values higher than 0.45. This linkage, Which was introduced into subtilisin 7140, has two residues that are absolutely conserved in the six sequences given in Table 4. The decreased stability associated with this protein is believed to be due to altering important interactions that have been conserved throughout evolution. Four other proteins, subtilisin 7136, 7122, 7115, and 7124 also contain disulfide linkages that involve the alteration of a conserved residue, and all of these, except 7136, have also been found to have decreased stability relative to the wild-type protein. These proteins, however, also have the highest RMS errors, so the reason for the observed decreased stability is not so apparent in these cases. It could derive from a combination of a poor fit (RMS error) and alteration of a conserved interaction.

The two proteins that contain disulfide bridges that are not comprised of conserved residues are subtilisin 7127 and 7123. These linkages also do not have too bad a fit (RMS error of 0.48 and 0.51, respectively). Both proteins were found to have stabilities close to that of the wild-type protein. The failure of the 24/87 linkage to stabilize subtilisin 7123 may be related to the poor short contacts noted in the table. The 1/78 linkage is complex because of the relatively high accessibility of the N-terminus. Complex thiol chemistry which included intermolecular crosslinking was found to occur for subtilisin 7127.

This invention is intended to be useful for the stabilization of many different kinds of proteins under sundry conditions. For example, the redesigned subtilisin BPN', described herein, has been used as an active ingredient in detergent formulations for the enhancement of detergent performance. Subtilisin-like proteases are currently used in detergent formulations to improve the removal of protein stains such as blood and milk from soiled fabrics or garments. These detergent formulations can often present conditions of pH, temperature, free metal ion concentrations, and detergent content (hydrophobicity) that do not favor the properly folded state of enzymes, i.e., subtilisin-like proteases. Therefore, the present invention provides protein enzymes of enhanced stability that may be used in these applications.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth is as follows in the scope of the appended claims.

What is claimed is:

1. A computer based method for evaluating a protein to determine whether said protein contains at least two target amino acid residues, replacement of at least one of which with a cysteine residue would be sufficient to permit formation of at least one potentially protein stabilizing disulfide bond, said bond containing two cysteine residues; said method comprising the steps of:
   (a) ascertaining relative three-dimensional positions of atoms of a pair of cysteine residues of a candidate disulfide bond;
   (b)
   (i) examining a candidate pair of amino acid residues of said protein to determine whether they contain atoms whose relative three-dimensional positions possess a geometric conformation which is similar to a geometric conformation possessed by atoms of said cysteine residues of said candidate disulfide bond (a);
   (ii) examining whether replacement of the candidate pair of amino acid residues of said protein by said cysteine residues of said candidate disulfide bond can be accommodated, to thereby permit the formation of a potentially stabilizing disulfide bond, without creating a conformation of said protein molecule having unacceptable steric hindrance;
   (c) repeating said examinations (b)(i) and (b)(ii) for each candidate pair of amino acid residues of said protein, and for each ascertained candidate disulfide bond (a);
   (d) ranking each candidate pair of amino acid residues of said protein for its capacity to be replaced with a potentially stabilizing candidate disulfide bond, without undesirably altering said tertiary conformation of the protein molecule; and
   (e) using said ranking (d) to identify a target pair of amino acid residues, replacement of at least one of which with a cysteine residue would be sufficient to permit formation of at least one potentially protein-stabilizing disulfide bond.

2. The method of claim 1 which additionally comprises:
   (f) identifying at least one target amino acid residue of said protein which could been placed by a cysteine residue thereby permitting the formation of a potentially protein-stabilizing disulfide bond; and
   (g) producing a protein molecule wherein said identified target amino acid residue has been replaced with a cysteine residue, said replacement permitting the formation of said potentially protein-stabilizing disulfide bone.

3. The method of claim 2 which additionally comprises:
   (h) forming the disulfide bond.

4. A computer based method for producing an engineered protein having a potentially protein-stabilizing disulfide bond which comprises:
   (a) using a computer based method to evaluate structure of said protein to determine whether said protein contains at least two target amino acid residues replacement of at least one of which with a cysteine residue would be sufficient to permit formation of at least one potentially stabilizing disulfide bond; said method comprising the steps:
   (1) examining each selected pair of amino acids in said protein to determine if they contain atoms whose relative three-dimensional positions possess a geometric conformation similar to a geometric conformation possessed by atoms of a disulfide bond.
   (2) examining any pair of amino acids found to contain said certain atoms identified in step (1) to determine whether said disulfide bond can be accommodated without creating unacceptable steric hindrance,
   (3) permitting an expert operator (i) to view any possible disulfide bond which can be accommodated without altering a tertiary conformation of said protein, and (ii) to rank said viewed possible disulfide bond from most likely to stabilize an engineered protein to least likely to stabilize said protein, and
   (4) evaluating said ranked possible disulfide bond according to expert rule criterion; and
   (b) producing an engineered protein molecule wherein at least one of said target amino acid residues has been replaced by a cysteine residue, said replacement permitting the formation of a potentially protein-stabilizing disulfide bond.

5. The method of claim 4 wherein said expert rule criteria of step (4) comprises the steps:
   (a) evaluating a possible disulfide linkage to determine whether formation of said linkage would require loss of an evolutionally conserved amino acid residue; or
   (b) evaluating a possible disulfide linkage to determine whether formation of said linkage would result in loss of a favorable hydrophobic interaction.

6. A protein of increased stability, wherein said protein is produced through the use of a computer based method for evaluating said protein to determine whether said protein contains at least two target amino acid residues, replacement of at least one of which with a cysteine residue would be sufficient to permit formation of at least one potentially protein-stabilizing disulfide bond, said bond containing two cysteine residues; said method comprising the steps of:
   (a) ascertaining relative three-dimensional positions of atoms of a pair of cysteine residues of a candidate disulfide bond;
   (b)
     (i) examining a candidate pair of amino acid residues of said protein to determine whether they contain atoms whose relative three-dimensional positions possess a geometric conformation which is similar to a geometric conformation possessed by atoms of said cysteine residues of said candidate disulfide bond (a);
     (ii) examining whether replacement of the candidate pair of amino acid residues of said protein by said cysteine residues of said candidate disulfide bond can be accommodated, to thereby permit the formation of a potentially stabilizing disulfide bond, without undesirably altering a tertiary conformation of said protein;
   (c) repeating said examinings (b)(i) and (b)(ii) for each candidate pair of amino acid residues of said protein, and for each ascertained candidate disulfide bond (a);
   (d) ranking each candidate pair of amino acid residues of said protein for its capacity to be replaced with a potentially stabilizing candidate disulfide bond, without undesirably altering the tertiary conformation of the protein molecule;
   (e) using said ranking (d) to identify a target pair of amino acid residues, replacement of at least one of which with a cysteine residue would be sufficient to permit formation of at least one potentially protein-stabilizing disulfide bond;
   (f) identifying at least one target amino acid residue of said protein which could be replaced by a cysteine residue thereby permitting the formation of a potentially protein-stabilizing disulfide bond;
   (g) producing a protein molecule wherein said identified target amino acid residue has been replaced with a cysteine residue, said replacement permitting the formation of said potentially protein-stabilizing disulfide bond, and
   (h) forming the disulfide bond, to thereby form said protein of increased stability.

7. A nucleic acid sequence which encodes the protein of claim 6.

8. The nucleic acid of claim 7 wherein said nucleic acid is DNA.

9. The nucleic acid of claim 7 wherein said nucleic acid RNA.

10. The protein of claim 6 wherein said protein is selected from the group consisting of an enzyme and a binding protein.

11. The protein of claim 10 wherein said protein is a binding protein.

12. The binding protein of claim 11 wherein said binding protein is a DNA binding protein.

13. A nucleic acid sequence which encodes the binding protein of claim 12.

14. The binding protein of claim 11 wherein said binding protein is selected from the group consisting of receptor binding proteins, hormone binding proteins, antigen binding proteins and hapten binding proteins.

15. A nucleic acid sequence which encodes the binding protein of claim 14.

16. A nucleic acid sequence which encodes the binding protein of claim 11.

17. The protein of claim 10 wherein said protein is an enzyme.

18. A nucleic acid sequence which encodes the enzyme of claim 17.

19. The enzyme of claim 17 wherein said enzyme is a protease.

20. The protease of claim 19 wherein said protease is a serine protease homologous to subtilisin.

21. The protease of claim 20 wherein said protease contains at least one disulfide bond at a position determined by:
   (a) obtaining the amino acid sequence of said protease;
   (b) aligning the amino acid sequence of said protease with the amino acid sequence of subtilisin to maximize amino acid homology; and
   (c) determining the position of said disulfide bond by identifying amino acid positions of said protein which have a geometry similar to at least one disulfide bond selected from the group consisting of:
     (i) a disulfide bond between residues 22 and 87 of said subtilisin; or
     (ii) a disulfide bond between residues 206 and 216 of said subtilisin.

22. A nucleic acid sequence which encodes the protease of claim 19.

23. The protease of claim 19 wherein said protease is subtilisin.

24. The subtilisin of claim 23 wherein said subtilisin is selected from the group consisting of subtilisin 7159, subtilisin 8307, subtilisin 7181, and subtilisin 8310.

25. The subtilisin of claim 23 wherein said subtilisin contains at least one disulfide bond selected from the group consisting of:
   (a) a disulfide bond between residues 22 and 87; and
   (b) a disulfide bond between residues 206 and 216.

26. A method for improving the removal of a proteinaceous stain on a fabric comprising adding the subtilisin of any one of claims 23, 24, 25 to a washing preparation and cleaning said stained fabric with said washing preparation.

27. A nucleic acid sequence which encodes the subtilisin of claim 23.

28. A nucleic acid sequence which encodes the subtilisin of claim 24.

* * * * *